(12) United States Patent
Jedamzik et al.

(10) Patent No.: US 10,012,562 B2
(45) Date of Patent: Jul. 3, 2018

(54) METHOD FOR DETERMINING TIME-DELAYED CHANGES OF TEMPERATURE-DEPENDENT OR STRESS-DEPENDENT PHYSICAL QUANTITIES OF A GLASS OR A GLASS CERAMIC

(71) Applicant: SCHOTT AG, Mainz (DE)

(72) Inventors: Ralf Jedamzik, Griesheim (DE); Clemens Kunisch, Arnsheim (DE); Thoralf Johansson, Nieder-Olm (DE)

(73) Assignee: SCHOTT AG, Mainz (DE)

( * ) Notice: Subject to any disclaimer, the term of this patent is extended or adjusted under 35 U.S.C. 154(b) by 488 days.

(21) Appl. No.: 14/437,229

(22) PCT Filed: Oct. 24, 2013

(86) PCT No.: PCT/EP2013/072260
§ 371 (c)(1),
(2) Date: Apr. 21, 2015

(87) PCT Pub. No.: WO2014/064189
PCT Pub. Date: May 1, 2014

(65) Prior Publication Data
US 2015/0285707 A1    Oct. 8, 2015

(30) Foreign Application Priority Data

Oct. 24, 2012   (DE) .................. 10 2012 110 177
Aug. 15, 2013   (DE) .................. 10 2013 108 865

(51) Int. Cl.
*G01N 25/00*    (2006.01)
*G01N 3/00*    (2006.01)
(Continued)

(52) U.S. Cl.
CPC .......... *G01M 11/005* (2013.01); *G01N 19/00* (2013.01); *G01N 25/02* (2013.01); *G01N 33/386* (2013.01); *G02B 1/00* (2013.01); *G02B 5/08* (2013.01)

(58) Field of Classification Search
USPC .................................................. 374/46, 107
See application file for complete search history.

(56) References Cited

U.S. PATENT DOCUMENTS 6,007,240 A    12/1999   Price
7,722,246 B1 *   5/2010   Carty ..................... G01N 25/16
                                                        252/960

(Continued)

OTHER PUBLICATIONS

International Search Report dated Jan. 20, 2014 for corresponding International Application No. PCT/EP2013/072260, 5 pages.

(Continued)

*Primary Examiner* — Mirellys Jagan
(74) *Attorney, Agent, or Firm* — Ohlandt, Greeley, Ruggiero & Perle, L.L.P.

(57) ABSTRACT

The invention generally relates to manufacturing or providing of glass or glass ceramic products. The invention is based on the object to allow for providing glass or glass ceramic products having very accurately characterized thermo-mechanical properties. For this purpose, a deformation of the glass or glass ceramic material is measured at least twice as a function of time with different rates of change in temperature or a mechanical stress. Based on the measurements, relaxation times and weighting factors are determined by modelling. Then, based on the relaxation times and weighting factors related to the distribution of relaxation processes occurring in the product, a time-delayed change of a temperature-dependent or stress-dependent physical quantity, such as thermal expansion or refractive index, is calculated as a function of a predefined (Continued)

temperature change or stress change. The invention is used for selecting during manufacturing suitable glass products exhibiting selected time-delayed properties.

20 Claims, 13 Drawing Sheets

(51) Int. Cl.
*G01K 3/00* (2006.01)
*G01M 11/00* (2006.01)
*G01N 25/02* (2006.01)
*G01N 33/38* (2006.01)
*G01N 19/00* (2006.01)
*G02B 1/00* (2006.01)
*G02B 5/08* (2006.01)

(56) References Cited

U.S. PATENT DOCUMENTS

| 2002/0048306 A1* | 4/2002 | Sauvant | G01N 25/12 374/21 |
| 2002/0196834 A1* | 12/2002 | Zaldivar | G01N 25/04 374/22 |
| 2012/0307860 A1* | 12/2012 | Zaldivar | G01N 25/04 374/16 |

OTHER PUBLICATIONS

Written Opinion of the International Searching Authority dated Jan. 20, 2014 for corresponding International Application No. PCT/EP2013/072260, 7 pages.

Jedamzik et al., "CTE Characterization of Zerodur for the ELT Century", Optical Materials and Structures Technologies IV, SPIE vol. 7425, 2009, pp. 742504-1 to 742504-11.

Jedamzik et al., "Zerodur for Stress Mirror Polishing", Optical Manufacturing and Testing IX, SPIE vol. 8126, 2011, pp. 812606-1 to 812606-11.

Jedamzik et al., "Zerodur for Stressed Mirror Polishing II", Modern Technologies in Space- and Ground-based Telescopes and Instrumentation II, SPIE vol. 8450, Sep. 13, 2012, pp. 84504P-1 to 84504P-10.

Jedamzik et al., "Modeling of the Thermal Expansion Behaviour of Zerodur at Arbitrary Temperature Profiles", Modern Technologies in Space- and Ground-based Telescopes and Instrumentation, SPIE vol. 7739, Jul. 16, 2010, pp. 77390I-1 to 77390I-12.

Lindig et al., "Thermal Expansion and Length Stability of Zerodur in Dependence on Temperature and Time", Applied Optics, vol. 24, No. 20, Oct. 15, 1985, pp. 3330 to 3334.

Soules et al., "Finite-Element Calculation of Stresses in Glass Parts Undergoing Viscous Relaxation", Journal of the American Ceramic Society, vol. 70, No. 2, Feb. 1, 1987, pp. 90 to 95.

\* cited by examiner

METHOD FOR DETERMINING TIME-DELAYED CHANGES OF TEMPERATURE-DEPENDENT OR STRESS-DEPENDENT PHYSICAL QUANTITIES OF A GLASS OR A GLASS CERAMIC

The invention generally relates to manufacturing or providing of glass or glass ceramic products. More particularly the invention relates to a method which permits to characterize, produce and/or select glass and glass ceramic products based on precisely defined thermo-mechanical properties.

Special glass and glass ceramic products that are developed and manufactured in customized manner for specific applications, have very different requirements placed thereon which have to be complied with by the manufactured glass or glass ceramic component due to the different application-specific requirements on thermo-mechanical quantities, such as thermal expansion and structural relaxation. Examples of such customized products include telescope mirror substrates and components for microlithography made of glass ceramics.

Glass ceramics exhibit low thermal expansion in different application temperature ranges depending on the product. ZERODUR, for example, was specifically developed for ultra-low thermal expansion in the room temperature range. Other glass ceramics, e.g. CERAN, exhibit low thermal expansion over a wider temperature range.

The coefficient of thermal expansion (CTE) of ZERODUR and other glass ceramics is specified as a mean CTE for a temperature range from 0° C. to 50° C. and is classified into several expansion classes. More strictly, however, this classification only applies to a predefined measurement procedure with precisely observed temperature rates and temperature holding times. This specification is sufficient for most applications, but gives an inaccurate picture of the material in detail. First, the expansion coefficient is not constant over the whole temperature range from 0° C. to 50° C., but is a function of temperature. Moreover, the expansion behavior is additionally a function of time, being known as hysteresis behavior. The temperature dependence and time dependence of the CTE is not a specific property of ZERODUR, but is an immanent feature of all glass ceramics. Hitherto, the hysteresis behavior could not be accounted for when specifying glass ceramics in applications, such as for ZERODUR, because a suitable method was lacking for specifying and predicting them.

Neither has it been possible to specify a delayed elasticity occurring when subjecting glass ceramics to a mechanical load. One problem therewith is that a calculation of structural and stress relaxation has only been known in the glass transition range, whereas for customized requirements the glass ceramics should be chosen based on their thermo-mechanical properties at room temperature. Therefore, there is a need for determining the behavior of glass or glass ceramic materials as a function of temperature and time, and/or the delayed elasticity as a function of stress and time, and to be able to produce or choose a glass or glass ceramic article based thereon.

In recent potential applications for ZERODUR, such as the giant telescope TMT (Thirty Meter Telescope) or the E-ELT of ESO (both of them "Extremely Large Telescopes"; ELTs) not only just the CTE (0° C.-50° C.) is being specified, for example, but the material behavior under the conditions of use at the future installation site of the telescope. This includes defined temperature ranges from −13° C. to +27° C., which are significantly different from the usual range of 0° C. to 50° C. Also, the rates of change in temperature during operation are in a range of <0.17 K/h and therefore are substantially smaller when compared to the typically measured rates of 36 K/h.

An object of the invention is to allow for providing glass or glass ceramic products having very accurately specified thereto-mechanical properties. This object is achieved by the subject matter of the independent claims. Advantageous embodiments and further modifications are set forth in the dependent claims.

The invention presented herein is based on the development of appropriate methods and models which permit highly accurate characterization of the thermo-mechanical properties of glasses and glass ceramics taking into account relaxation phenomena below the classic glass transition. In the following, the wording "below glass transition" (transformation temperature $T_g$ defined according to ISO 7884-8) refers to a temperature range below $T_g$ minus 100 K, where relaxation phenomena cannot be represented by models and techniques of glass transition physics. In the case of a glass ceramic, temperature $T_g$ is the glass transition temperature of the residual glass phase.

Previous models of structural and stress relaxation only enable to simulate relaxation processes in the glass transition range. The existence of relaxation processes at significantly lower temperatures has been known and can be measured. Although methods have been developed that increase the accuracy of measurement, phenomena of relaxation are however disregarded in evaluation and characterization of the affected material properties. A consequence thereof was that for a sufficiently good quantification of material properties, the exact application conditions (e.g. temperature-time history) needed to be represented in a measurement. This is not possible in many cases, for metrological reasons and due to lack of time. A suitable model for the relaxation phenomena mentioned above does not yet exist.

Therefore, differences between measurement conditions and conditions of use are generating significantly larger errors than could be assumed based on the measurement uncertainty. In particular, it has been unclear how relaxation phenomena mutually influence each other in different temperature ranges.

The invention also provides a method for predicting thermal expansion for $T<T_g-100$ K taking into account thermal history and freely selectable thermal conditions of use and the associated relaxation phenomena.

By now, thermal expansions have been characterized on the basis of a mean thermal expansion across a predefined temperature range measured by a measuring technique, the thermal conditions of use being significantly different from the measurement conditions. The method for predicting thermal expansion presently described overcomes this problem, i.e. the practical measuring method used permits to characterize material behavior so well that a significantly higher prediction accuracy is obtained.

The same applies to a prediction of delayed elasticity at temperatures below the glass transition taking into account the thermo-mechanical history and freely selectable thermo-mechanical conditions of use and the associated relaxation phenomena.

For this purpose, the invention provides a method for determining time-delayed changes of temperature-dependent or stress-dependent physical quantities of a glass or a glass ceramic, the determination being performed in a temperature range having an upper limit not higher than 100 K below the glass transition temperature (i.e. 100 K below the glass transition temperature or lower than 100 K below the glass transition temperature), wherein a deformation of the glass or glass ceramic material is measured at least twice, with different rates of change in temperature or a mechanical stress as a function of time, the measurements also being carried out at temperatures of not higher than 100 K below the glass transition temperature, and wherein a plurality of relaxation times of the glass or glass ceramic material are determined for a reference temperature, and weighting factors are determined, which represent a weight of the relaxation times in the relaxation of the glass or the glass ceramic. These relaxation times and weighting factors then permit to calculate a time-delayed change of a temperature-dependent or stress-dependent physical quantity as a function of a predefined temperature change or stress change.

The term "time-delayed change" in the sense of the invention refers to a change of the physical quantity, which does not occur instantaneously, but occurs after the temperature or mechanical stress has been changed. Preferably, the calculation is performed for a time or period which is at least 10 seconds, preferably at least 10 minutes following the change in temperature or mechanical stress.

The method is particularly suitable for predicting physical quantities in form of thermal or mechanical deformations of a glass or a glass ceramic. However, other physical quantities are also affected by the relaxation of the glass or glass ceramic material. These include heat capacity and also the refractive index.

The invention is generally suitable for calculating the following time-delayed changes:
- a change in length;
- a change in volume;
- a change in refractive index;
- a change in heat capacity;
- a change in shear modulus;
- a change in bulk modulus;
- a change in torsion modulus;
- a change in Young's modulus.

This allows to not only to calculate and predict the time-delayed changes, but also the corresponding absolute values of these quantities as a function of the change in temperature or mechanical stress.

The characterization of a time-delayed deformation as a physical quantity may be accomplished using one or more time-dependent deformation parameters of the material, which describe a deformation of the glass or the glass ceramic at temperatures of the glass or the glass ceramic which are at least 100 K below the glass transition temperature (i.e. not higher than 100 K below the glass transition temperature). The time dependence of these parameters may then be determined based on the determined relaxation times. For larger deviations of temperatures for which the time dependence of a physical quantity is to be calculated, such as the time-delayed deformation as mentioned before, a thermal displacement function may be determined in addition to the relaxation times and weighting factors. The displacement function specifies how the relaxation of the glass or glass ceramic material changes as a function of temperature. The displacement function does not only describe this dependence for deformations due to temperature changes, but more generally also for other physical quantities that depend on the relaxation state of the glass or glass ceramic, such as refractive index, shear or torsion modulus, and heat capacity.

A time-dependent deformation parameter refers to a physical quantity which affects the mechanical properties or the mechanical condition of the material depending on a time-dependent quantity. The mechanical condition includes the geometry of the article made from the glass or glass ceramic material, inter alia. An important mechanical condition, for example, is the size/shape of a glass or glass ceramic component. The geometrical dimensions of a component are affected by thermal expansion caused by the coefficient of expansion and a temperature change, the rate of change in temperature also having some influence on the coefficient of thermal expansion, as explained before with reference to the telescope mirror issues mentioned above. Accordingly, the coefficient of thermal expansion and physical quantities derived therefrom, in particular the dimensions of the component, are time-dependent deformation parameters. Elastic deformation under action of a force and the associated material properties such as shear modulus and bulk modulus are likewise time-dependent deformation parameters. Also suitable as a parameter are permittivity and/or mechanical internal friction of the material.

An accurate characterization of the glass or glass ceramic material in terms of its thermo-mechanical behavior over time then also permits to provide a glass or glass ceramic component that exhibits a precisely known and predictable long-term deformation when the component is subjected to temperature and/or force changes. In particular, the present invention also suggests a method for providing a glass or glass ceramic article exhibiting a predefined time-delayed thermal or mechanical deformation. For this purpose:
- an allowable range of values of a time-delayed thermal or mechanical deformation in a temperature range with an upper limit of not higher than 100 K below the glass transition temperature is predefined;
- a deformation of a glass or glass ceramic material is measured at least twice as a function of time with different rates of change in temperature or in a mechanical stress; wherein
- the measurements are performed at temperatures of at least 100 K below the glass transition temperature (i.e. not higher than 100 K below the glass transition temperature); and wherein
- a plurality of relaxation times of the glass or glass ceramic material are determined for a reference temperature, and weighting factors are determined, which represent a weight of the relaxation times in the relaxation of the glass or the glass ceramic.
- Based on the relaxation times and weighting factors, a time-delayed change of a temperature-dependent or stress-dependent time-delayed deformation is then calculated as a function of a predefined temperature change or stress change.

In a non-isothermal case, i.e. in case of larger deviations in temperature from the reference temperature, for which deviations the deformation is to be calculated, parameters of the thermal displacement function are additionally determined according to one embodiment of the invention.

The thermal or mechanical deformation is extrapolated to the predefined allowable range of values using the one or more relaxation time(s); and a comparison is made as to whether the extrapolated thermal or mechanical deformation is within the range of values.

Then, the glass or glass ceramic material is chosen when the extrapolated value of time-dependent thermal or mechanical deformation is within the allowable range of values, or an article is rejected, when the predefined range of values is not met.

In one embodiment of the invention, providing the glass or glass ceramic article comprises selective manufacturing of the glass or glass ceramic article for the predefined range of values by adjusting the manufacturing conditions of the glass or glass ceramic production in a manner so that the range of values is observed, or obtained. This may be achieved in simple manner by interpolation or extrapolation of production parameters. Production parameters particularly relevant include the composition, in case of glass ceramics additionally the temperature-time profile of ceramization. If, for example, two glass ceramics are available which differ in terms of ceramization conditions and/or composition and which exceed or fall below the predefined allowable range of values, a glass or a glass ceramic may selectively be produced by interpolating the composition and/or the ceramization conditions in order to obtain the specified range of values. If both of the existing materials fall below or exceed the predefined allowable range of values, extrapolation may be made towards the smaller deviation among the two materials, to obtain the range of values. It will of course be advantageous to verify the admissibility of the range of values in the newly manufactured glass or glass ceramic material by measuring the relaxation times and weighting factors according to the invention. In the manufacture of glass ceramics, the relationship between the retention time at the maximum temperature of ceramization and the time-dependent coefficient of thermal expansion resulting from the measurement according to the invention may be used for this purpose in order to selectively set a specific time-dependent coefficient of thermal expansion in the manufacture of the glass ceramic.

The invention will now be explained in more detail with reference to the accompanying drawings, wherein.

Figure 17:
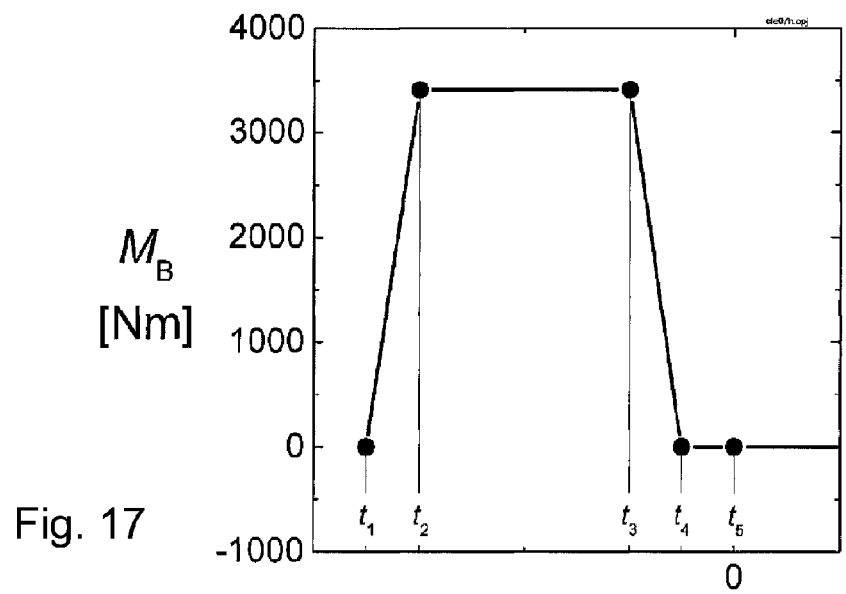
Figure 18:
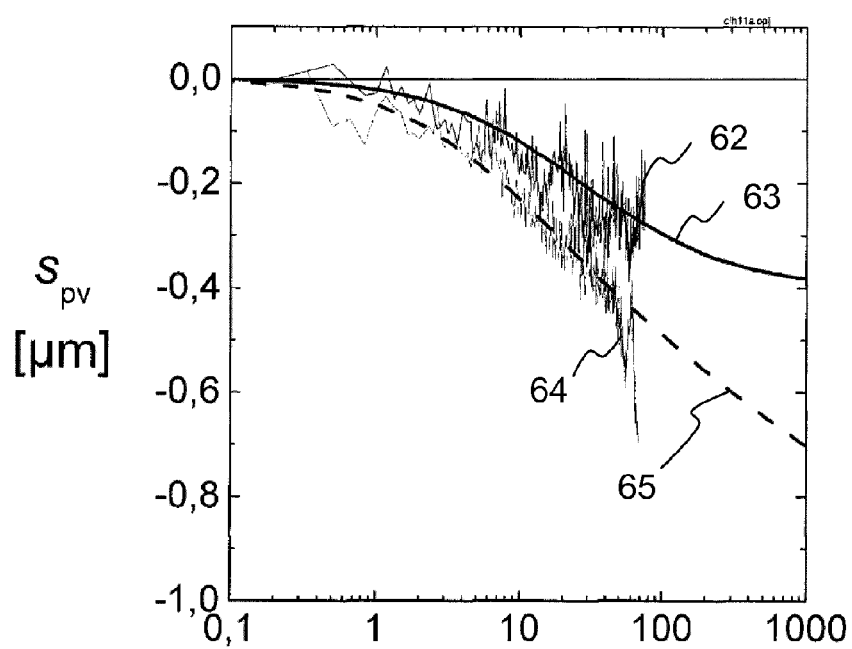
Figure 19:
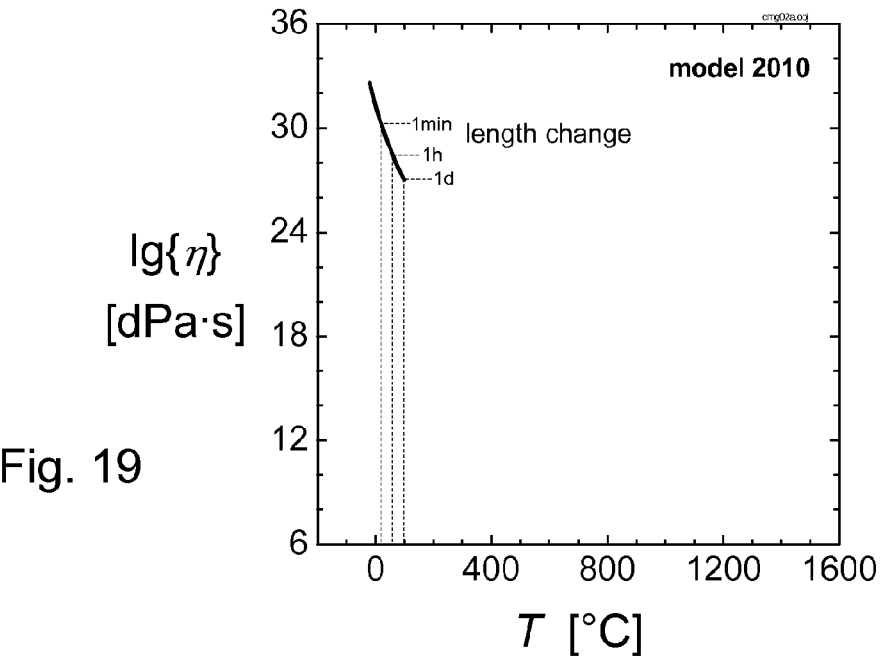
Figure 20:
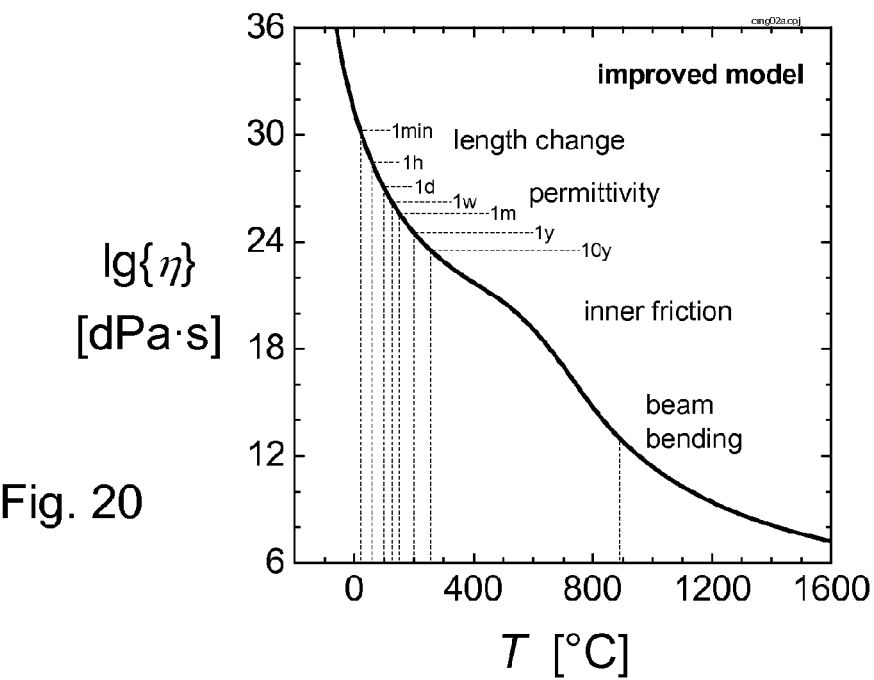
Figure 21:
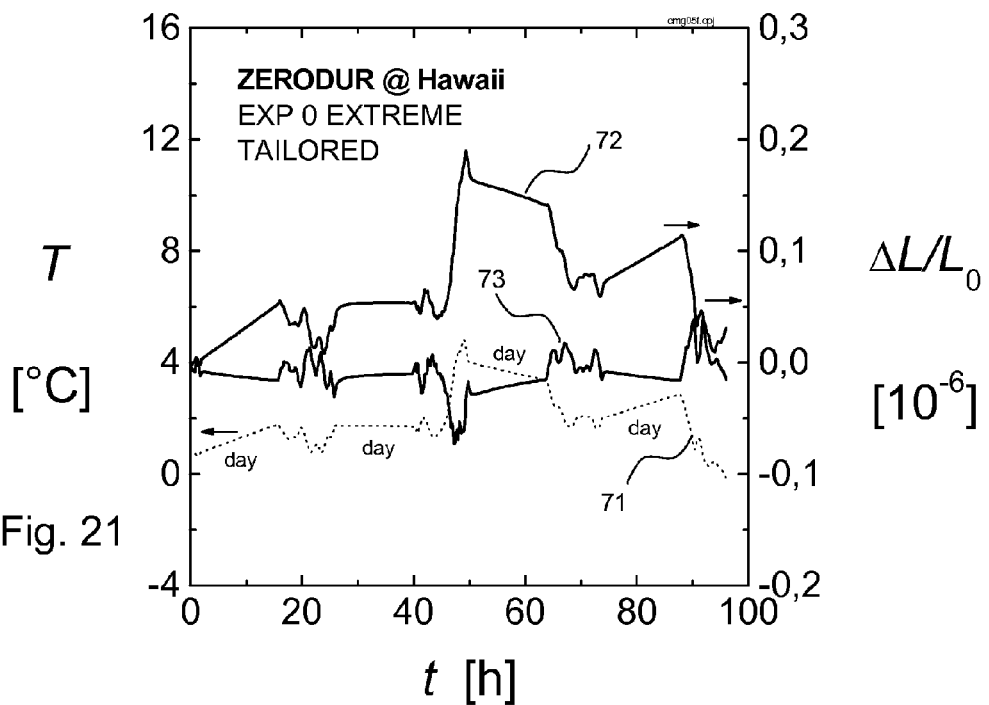
Figure 22:
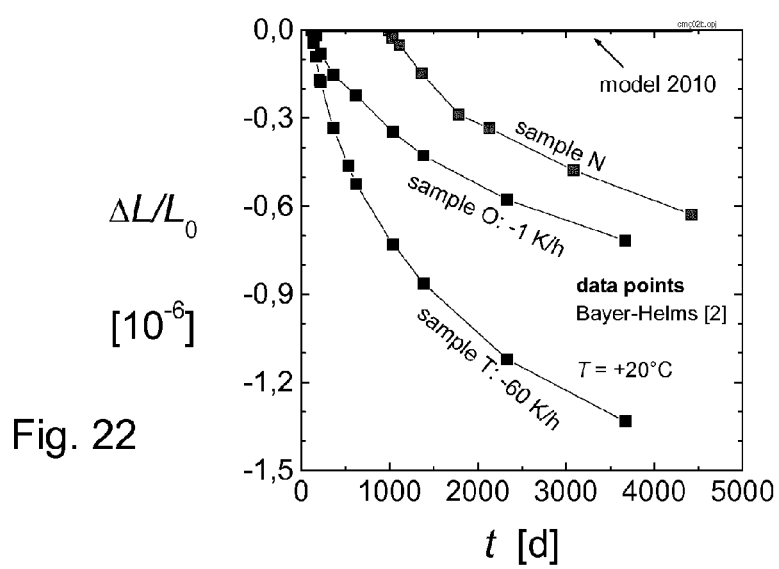

FIGS. 16A to 16D schematically illustrate glass or glass ceramic samples in different configurations, with forces acting thereon for measuring component deformations;

FIG. 17 shows time variation of a mechanical stress in form of a deflection moment applied in stress mirror polishing of a telescope mirror;

FIG. 18 shows time-dependent maximum bowl-shaped deflection $s_{pv}$ of a telescope mirror, as measured and as calculated;

FIG. 19 shows viscosity as a function of temperature for low temperatures;

FIG. 20 shows viscosity as a function of temperature for the entire relevant temperature range;

FIG. 21 shows time variation of thermal expansion of two samples under temperature conditions in Hawaii;

FIG. 22 shows the relative change in length of different samples over time; and

Figure 23:
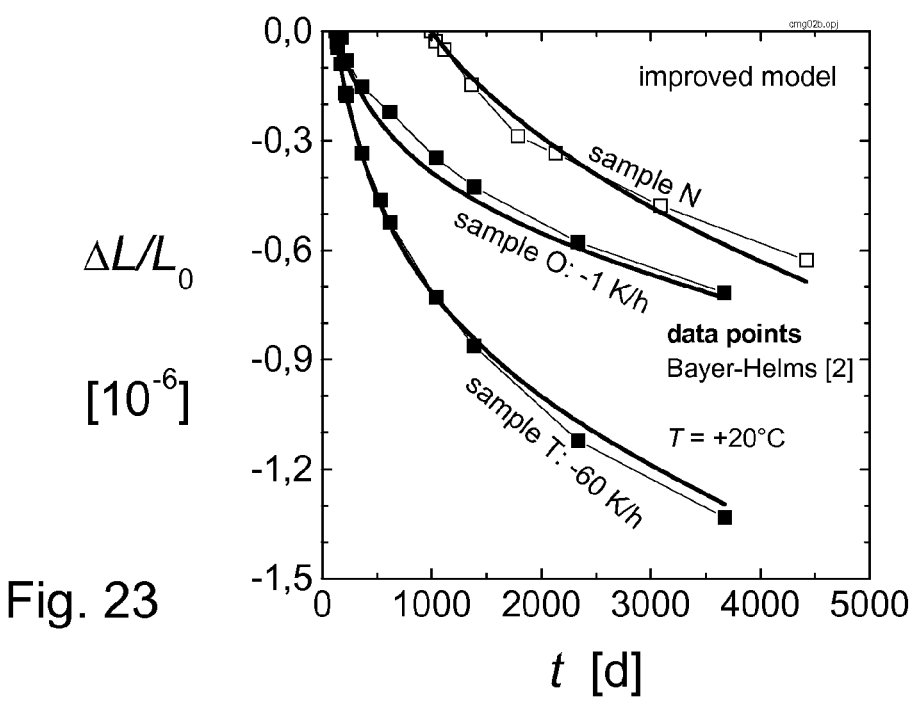

FIG. 23 compares the relative change in length of different samples over time, as measured and as modeled.

Mathematical modeling of relaxation of the atomic structure in the glass transition range (around transition temperature $T_g$ defined by ISO 7884-8) and of stress relaxation is known and is employed for mathematical modeling of thermo-mechanical processing methods of glass in the glass manufacturing and processing industry. The models are implemented in FEM calculation software (e.g. ANSYS). From O. S. Narayanaswamy, "A model of structural relaxation in glass", J. Am. Ceram. Soc. 54, 491-498 (1971), a model is known, which allows to describe these structural relaxations in the glass transition temperature $T_g$ range in a sufficiently good modeling quality. Structural relaxation is seen as a process of transition from a non-equilibrium into an equilibrium of the glass structure (atomic rearrangement processes).

Figure 1:
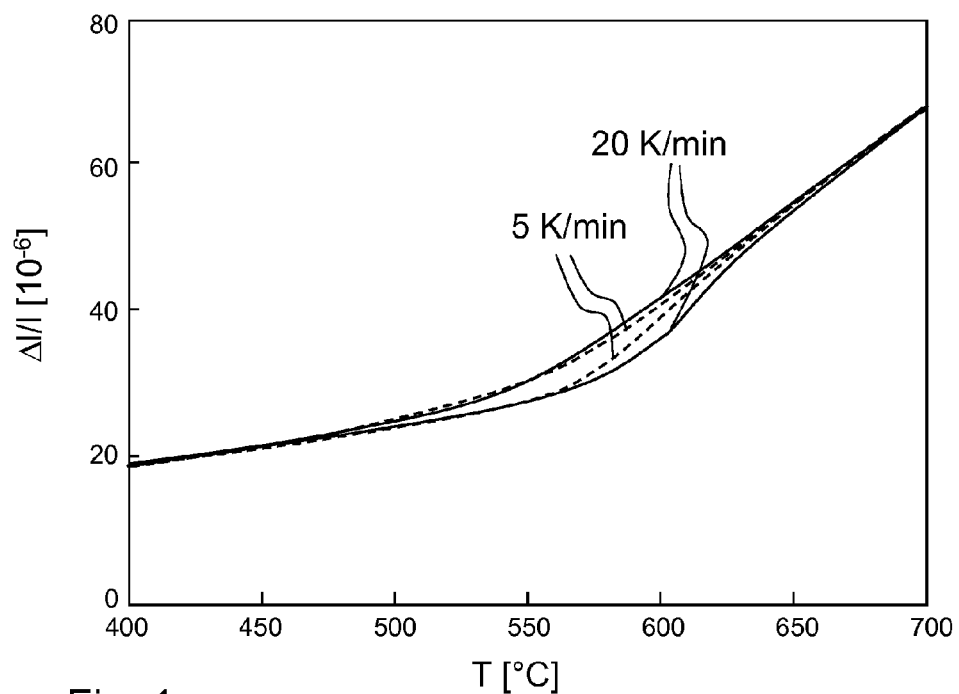
FIG. 1 shows a hysteresis of change in length of a glass in the range of glass transition.

Glasses are distinguished by the fact that a non-equilibrium state can be frozen. Depending on thermal conditions (fast/slow cooling), the glass is frozen in different states. A characteristic feature of relaxation processes are hystereses in expansion measurements, which are caused by the different relaxation behavior during heating/cooling. FIG. 1 shows two exemplary hysteresis curves of relative thermal expansion $\Delta l/l$ of a glass for two different rates of change in temperature of 5 K per minute and 20 K per minute. In the range of glass transition where the slope of temperature-dependent relative thermal expansion $\Delta l/l$ changes, a hysteresis is clearly visible and can be described by the model mentioned above. At temperatures of 100 K or more below glass transition, however, hysteresis is very small and is no longer described by the model. Nevertheless, changes in length which depend on the rate of change in temperature may be relevant also in this low temperature range, for example when a very precise knowledge of length dimensions is beneficial.

A quantitative parameter for characterizing the non-equilibrium state is the so called fictive temperature. This state variable is a measure for the glass structure (atomic structure), and in a state of equilibrium (e.g. above the glass transition range) it takes the same value as the actual temperature. Freezing of the structure changes thermo-mechanical properties of the material.

These include for example the coefficient of thermal expansion (CTE) and the specific heat capacity of glasses and glass ceramics.

According to one embodiment of the invention, therefore, the relaxation times are used for determining the fictive temperature, or, as will be explained below, a corresponding state variable and time dependence thereof. The determination of fictive temperature and of a time-delayed deformation will now be described in detail.

A deformation ε generally comprises a thermal part $\varepsilon_{th}$ and a mechanical part $\varepsilon_{mech}$:

$$\varepsilon = \varepsilon_{th} + \varepsilon_{mech}. \qquad (1)$$

Within a time interval Δt, the thermal part of expansion changes $$\Delta\varepsilon_{th} = \alpha_s(T)\cdot\Delta T + \alpha_f(T_f)\cdot\Delta T_f, \qquad (2)$$

with linear coefficients of thermal expansion $\alpha_s$ of an immediate change in length (as a function of actual temperature T), and $\alpha_f$ of a time-delayed change in length (as a function of fictive temperature $T_f$). The mechanical part of elongation $\varepsilon_{mech}$ changes according to Hooke's law, with time-dependent bulk modulus K(t), and time-dependent shear modulus G(t), see Equations (12) to (16) below.

The fictive temperature as a state variable is the weighted sum of n fictive temperatures $$T_f = \sum_k^n w_k T_{f,k} \qquad (3)$$

as an image of several individual processes, with weighting factors $w_k$ and their sum $$\sum_k^n w_k = 1 \qquad (4)$$

and relaxation function $$\Psi_{str} = \sum_k^n w_k \cdot \exp\left\{-\frac{t}{\tau_k}\right\} \qquad (5)$$

of the glass structure, a Kohlrausch function. The rate of change of the individual fictive temperatures $$\frac{\partial T_{f,k}}{\partial t} = \frac{T - T_{f,k}}{\tau_k} \qquad (6)$$

depends on a relaxation time $$\tau_k = \tau_{ref,k} \cdot a_T \qquad (7)$$

with the logarithm of the thermal displacement function $$\log_{10}\{a_T\} = B\cdot\left(\frac{1-C}{T} + \frac{C}{T_f} - \frac{1}{T_{ref}}\right). \qquad (8)$$

Equation (8) is given as a common logarithm. However, the choice of the basis is arbitrary, since logarithms can be converted into each other. The displacement function according to equation (8) corresponds to the displacement function of the so-called Tool-Narayanaswamy model from the above-mentioned publication O. S. Narayanaswamy: "A model of structural relaxation in glass", J. Am. Ceram. Soc. 54, 491-498 (1971).

The thermal displacement function is used for time-temperature superposition. In the case of sufficient validity of the time-temperature superposition, processes in the material which proceed very slowly or very quickly at room temperature, are equivalent to processes that last a few minutes at high or low temperatures. If a material behaves in this manner, then an appropriate displacement function allows for model predictions for both low and high temperatures as well as for very slow and very fast processes in the material or its response to application conditions/impacts of use.

Instead of equation (8), the following equations may be used in the glass transition region:

$$\log_{10}\{a_T\} = \frac{B}{T(1-C/T_f)} - \frac{B}{T_{ref} - C} \qquad (9)$$

$$\log_{10}\{a_T\} = \frac{B}{T}\exp\left\{\frac{C}{T_f}\right\} - \frac{B}{T_{ref}}\exp\left\{\frac{C}{T_{ref}}\right\} \qquad (10)$$

$$\log_{10}\{a_T\} = \left(\frac{B}{T}\right)^c - \left(\frac{B}{T_{ref}}\right)^c. \qquad (11)$$

These provide very similar but not identical results. Which one of equations (8) to (11) fits better to the measurement results is often not clearly decidable in terms of measurement accuracy.

The subscript "ref" in equations (8) to (11) represents the reference state for a fixed chosen temperature, $T_{ref}$.

In the equations mentioned above, weighting factors $w_{str,k}$, relaxation times $\tau_{str,ref,k}$, and factors B, C of the displacement function are model parameters which may be determined by fitting the model of the above equations to deformation measurements.

In analogy to the model approach of fictive temperature, the bulk modulus $$K(t) = K_0 \cdot \Psi_K \qquad (12)$$

($K_0$ = instantaneous bulk modulus) relaxes according to its relaxation function:

$$\Psi_K = w_{K,\infty} + \sum_k^{nK} w_{K,k} \cdot \exp\left\{-\frac{t}{\tau_{K,k}}\right\} \qquad (13)$$

wherein $\sigma_{K,k}$ denote the relaxation times of the bulk modulus. For the sum of weighting factors $w_{K,k}$ the following applies:

$$w_{K,\infty} + \sum_k^{nK} w_{K,k} = 1 \qquad (14)$$

with the limit value $$w_{K,\infty} = \frac{K_\infty}{K_0} \qquad (15)$$

for very long times. The shear modulus relaxes according to the same model approach, with the difference that for sufficiently high temperatures and sufficiently long times the limit $G_\infty$ approaches zero, i.e.

$$w_{G,\infty} \approx 0 \qquad (16)$$

can be used. The displacement function is the same as with the fictive temperature.

Relaxation processes in glasses and glass ceramics also occur beyond the relaxation processes detectable with the mathematical models of glass transition. This effect in glasses has long been known, for example in so-called thermometer glasses. It is also referred to as "depression of the zero point" and is based on a mixed alkali effect. Often the order of magnitude of this effect is below a required accuracy and is ignored in the measurement.

Figure 2:
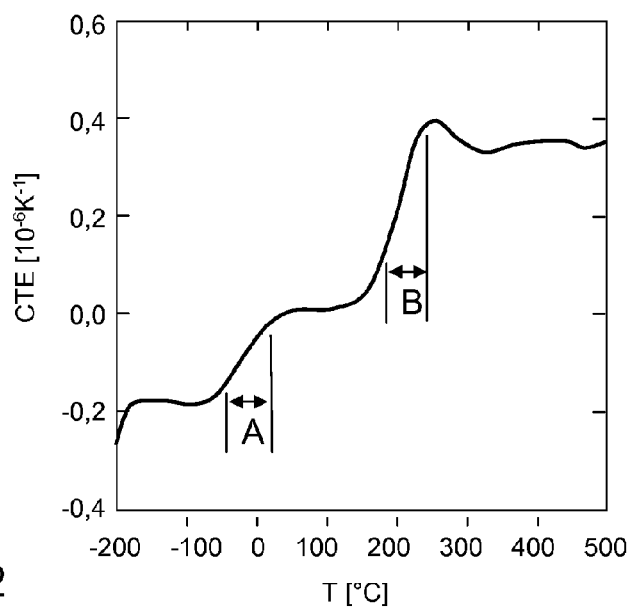
FIG. 2 shows the linear coefficient of thermal expansion of a ZERODUR glass ceramic.

In glasses and glass ceramics with very high precision requirements placed thereon (e.g. so called zero-expansion materials) the relaxation effects have been known qualitatively for a long time and are indirectly accounted for in the production of glasses, by preferably defined reproducible production conditions. For zero-expansion material (e.g. ZERODUR), the coefficient of thermal expansion (CTE) is defined for the temperature range from 0° C. to 50° C. and is classified into different classes. More strictly, however, this classification only applies to a single defined measurement procedure with precisely observed temperature rates and temperature holding times. This specification is sufficient for some applications, but gives an incomplete picture of the material in detail. For example, FIG. 2 shows the linear coefficient of thermal expansion CTE of a zero-expansion material, in particular a ZERODUR glass ceramic, as it has been specified so far for characterizing such materials. The linear coefficient of expansion as shown in FIG. 2 neglects the time dependence of thermal expansion caused by relaxation processes, which is detected according to the present invention by determining a plurality of relaxation times and the displacement function of the material.

First, the expansion coefficient is not constant across the entire temperature range from 0° C. to 50° C., but is a function of temperature. Second, the expansion behavior is additionally a function of time, which has already been described by the term of hysteresis behavior in O. Lindig, W. Pannhorst: "Thermal expansion and length stability of Zerodur in dependence on temperature and time", Appl. Opt., Vol. 24, No. 20 (1985). This means for example that during cooling and heating the curves in temperature ranges A and B shown in FIG. 2 will not exactly overlie each other but have slightly different temperatures. A method for quantitative characterization of the relaxation processes and for calculating the properties depending on the relaxation processes (thermal expansion, thermal capacity, stresses, deformations) did not exist so far. Some approaches to understand the relaxation phenomena (F. Bayer-Helms, H. Darnedde, G. Exner: Metrologia 21, 49 57 (1985), and R. Schödel, G. Bönsch: Precise interferometric measurements at single crystal silicon yielding thermal expansion coefficients from 12° C. to 28° C. and compressibility, Proc. Spie (2001)) are limited to a phenomenological description (interpolation of measurement results) of relaxation and do not offer any model approach for quantitatively describing changes of properties under conditions different from those during the measurement, by extrapolation or prediction, or for determining material characteristics.

The "descriptive" measurement procedures previously used result in misunderstandings, in particular when comparing different materials in view of application ranges, since for example the hysteresis of thermal expansion observed in a measurement affects material performance under real operating conditions far less than could be assumed based on the measurements.

The invention now enables, inter alia, to calculate the characteristic curve of the coefficient of thermal expansion of ZERODUR for customized temperature intervals and temperature rates. A result thereof with regard to specification considerations in the Extremely Large Telescope projects is that it is now possible to choose the material much more specifically in terms of conditions of use of the glass ceramic article, and consequently better performance can be provided than before.

The invention also enables to describe and predict time-delayed elasticity of glass or glass ceramic components, such as of ZERODUR, under mechanical load. For example, a stress relaxation behavior determined according to the invention can be taken into account in stress mirror polishing, and in this way the dimensional stability of large telescope mirrors can be improved. Also, the time-dependent dimensional stability of high-precision mechanical components under their own weight and under mechanical stress can be predicted and can be taken into account appropriately when using the components.

Figure 3:
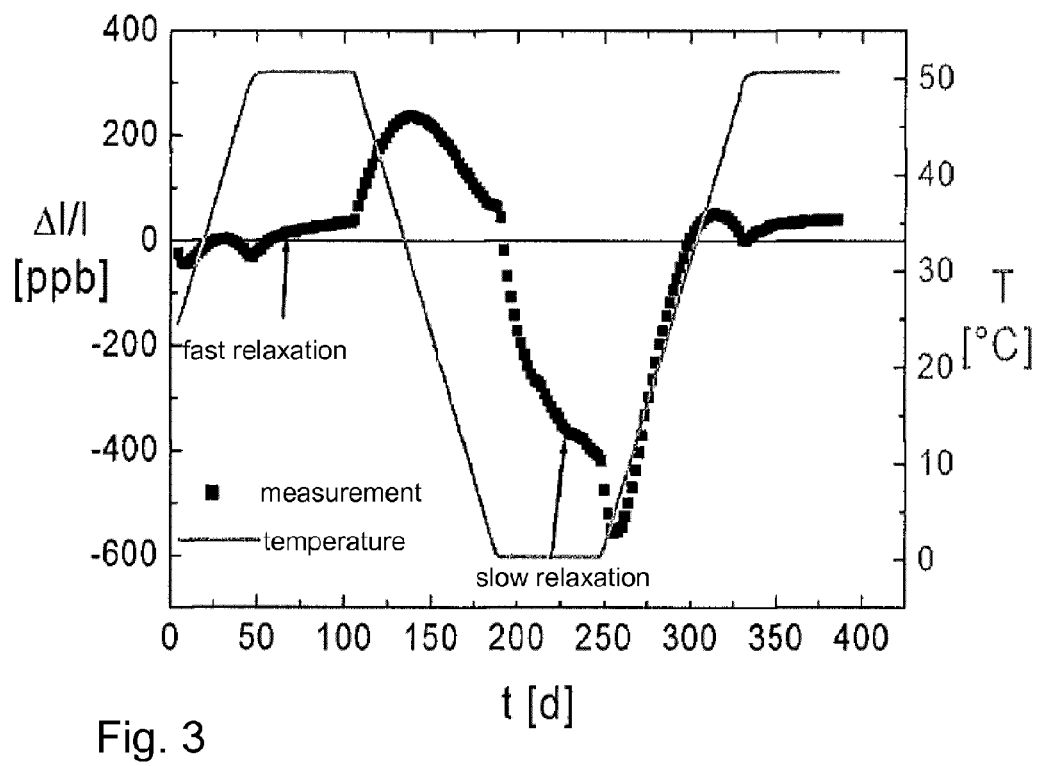
FIG. 3 shows an example of a measurement of thermal expansion from which the relaxation spectrum may be generated.

FIG. 3 shows an example of a measurement of thermal expansion for temperatures between 0° C. and 50° C., from which the typical relaxation curve of a glass or glass ceramic body may be determined. The measurement was carried out on a ZERODUR glass ceramic body. Illustrated therein is, on the one hand the temperature profile with the temperature scale on the right hand ordinate axis, and on the other the deformation in form of a change in length $\Delta l/l$ on the left hand ordinate axis, in each case as a function of time. The different relaxation rate at different temperatures is clearly visible. Thus, cyclic thermal ancillary conditions will result in hysteresis phenomena such as those observed in the glass transition range (see FIG. 1) even below the glass transition range. The area of such hysteresis may be of different size and will be influenced by the material composition and thermal ancillary conditions (heating/cooling rates). According to one embodiment of the invention, a characterization of the glass or glass ceramic material is to allow for a prediction of such hysteresis and relaxation phenomena.

When searching for a model of structural relaxation for temperatures below glass transition, it has surprisingly been found that a model in form of an extension of known relaxation models (e.g. Tool-Narayanaswamy) to other temperature ranges enables to provide a sufficiently precise match between model and measurement. This however only when introducing new state variables $T_{fx}$, X={A, B, C, . . . }, by which relaxation in temperature ranges A, B, C, . . . can be characterized. These state variables take over the function the fictive temperature has in the glass transition range.

However, they differ both in magnitude and in the effect on thermo-mechanical properties. Below, the state variables $T_{fx}$, X={A, B, C, . . . } will be considered as being independent of each other. For the sake of simplicity, in the context of the invention these state variables are also referred to as fictive temperature.

The model will be explained with reference to the temperature range A: −10° C. to 50° C., but can be transferred to any relevant temperature range between 10 K and $T_g$−100 K, in which relaxation processes are observed. For example, a narrower temperature range relevant for the characterization of thermo-mechanical properties, for which the present invention may be used for predicting deformations, is a range between 150 K and $T_g$−200 K. The majority of relevant applications of glass or glass ceramic materials falls into this range. More preferably, a prediction is made for temperatures of −50° C.<T<+80° C., most preferably for temperatures of −20° C.<T<+50° C.

For applications in outer space, for example for predicting and considering time-delayed thermal expansions or expansions under mechanical load, even very low temperatures are relevant.

In the model, a thermo-mechanical property p associated to relaxation (e.g. thermal expansion) depends on the temperature T and state variables $T_{fX}$, X={A, B, C, ... }: p=p(T, $T_{fA}$, $T_{fB}$, ... ). If the application temperature range is limited to a single relaxation temperature range (as is assumed below), the dependence can be reduced to the temperature and one state variable: p=p(T, $T_{fA}$).

The change in the property or physical quantity p (e.g. thermal expansion, enthalpy, density) may for example be represented as a polynomial of temperature T and state variable $T_{fA}$:

$$\Delta p(T, T_{fA}) = p_s(T)\Delta T + p_f(T_{fA})\Delta T_{fA} = \Sum_{i=0}^{n} p_{s,i} T^i \Delta T + \Sum_{j=0}^{m} p_{f,j} T_{fA}^j \Delta T_{fA}. \quad (17)$$

Therein, $p_s(T)$ designates a specific change of the property or physical quantity per unit temperature (e.g. the specific coefficient of thermal expansion (CTE), or the specific heat capacity).

$\Delta T, \Delta T_{fA}$ designate the change in temperature, or in fictive temperature.

$p_f(T_{fA})$ in equation (17), accordingly, is the specific time-delayed change of the property or physical quantity per unit temperature.

$p_{0,i}$, $p_{1,j}$ in equation (17) are coefficients of the terms of the polynomial.

In the above equation, a change is to be understood as a change of the relevant quantities over time.

Relaxation is the result of a relaxation of state variable $T_{fA}$ which may be represented in the same manner as the fictive temperature of glass transition, as a spectrum of differently relaxing state variables $T_{fAi}$ with weighting factors $v_i$, and relaxation times $\tau_i$, similar to equation (6) given above:

$$\frac{dT_{f,A,k}}{dt} = \frac{T - T_{f,A,k}}{\tau_k} \quad (18)$$

According to the above equation (4) of the model for the range of glass transition, the sum of the weighting factors is equal to 1:

$$\sum_k^n w_k = 1, \quad (19)$$

wherein, again, the generalized Maxwell model can be used for relaxation function $\Psi(t)$:

$$\Psi(t) = \sum_k^n w_k \cdot \exp\left[-\frac{t}{\tau_k}\right]. \quad (20)$$

The spectrum of relaxation times represents the relaxation behavior of the state variables and may possibly also be described as a Kohlrausch function with few parameters.

The relaxation times are determined for a reference temperature $T_{ref}$ by suitable measurements with different rates of change in temperature or mechanical stress, and according to one embodiment of the invention the relaxation times are again a function of temperature, of the time-dependent state variables, weighting factors, and material constants B, C, according to the following two equations:

$$\tau_k(T) = \tau_k(T_{ref}) \cdot a_T \quad (21.1)$$

$$\log_{10}\{a_T\} = B \cdot \left(\frac{1-C}{T} + \frac{C}{T_f} - \frac{1}{T_{ref}}\right) \quad (21.2)$$

$$T_{fA} = \sum_{k=1}^{n} w_i T_{fAi}(t). \quad (22)$$

Equation (21.1) corresponds to equation (8), with the logarithm of the displacement function according to equation (21.2). Equation (22) corresponds to equation (3), wherein according to equation (22) the state variable $T_{fA}$ results as a sum of products of weighting factors $w_i$ and state variables $T_{fAi}$, similar to the fictive temperature.

With these equations and a suitable numerical calculation algorithm it is possible to calculate the state variables and material properties (as a function of the temperature and state variable) when the parameters of the material model of relaxation are known.

According to one embodiment of the invention, therefore, weighting factors $w_k$ and relaxation times $\tau_k(T_{ref})$ at a reference temperature $T_{ref}$ are determined at least twice, at different rates of change in temperature or a mechanical load, and therefrom a plurality of temperature-dependent relaxation times $\tau_k(T)$ and parameters B, C in equation (21.2) and state variables $T_{fA}$, $T_{fAi}$ are determined by fitting the parameters of equations (17), (18), (19), (20), (21.1), (22) to the measured values. From these equations with known parameters, a time-dependent change of the physical quantity may then be determined, for example a time-dependent deformation of the glass or glass ceramic material, or a change of the refractive index when subjected to a temperature change or to a mechanical stress varying over time, or more generally a quantity related to a deformation, as a function of the change in temperature or of a mechanical stress over time. The model according to equations (17) through (22) is particularly suitable for limited temperature ranges comprising not more than 200 K, for example for temperatures close to room temperature. For example, a good prediction of the time-dependent change of a physical quantity, such as a deformation caused by thermal expansion, can be made in a temperature range between −50° C. and +80° C., in particular if temperature $T_{ref}$ is in this range. Instead of the thermal displacement function according to equation (21.2), a different thermal displacement function can be used. Suitable displacement functions will be explained further below.

According to yet another embodiment of the invention, parameters $T_{fA}$, $T_{fAk}$, $w_k$, $\tau_k(T_{ref})$ of equations (18) to (22) are used with equation (17) to determine a time-dependent deformation of the glass when subjected to a time-varying temperature or mechanical stress at temperatures ranging from −50° C. to +80° C.

Figure 4:
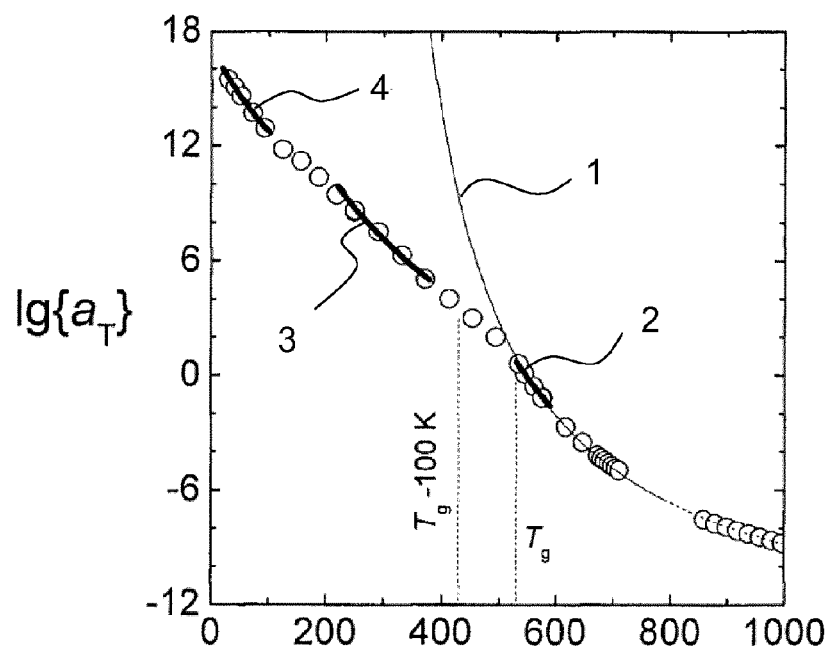
FIGS. 4 and 5 show measured values of decadic logarithm of the thermal displacement function and various displacement functions fitted to the measured values.

The model approaches of the displacement function according to the above equations (8) through (11) provide a sufficiently good agreement between measurement and model for temperatures in the glass transition range, i.e. in a temperature range of $T_g \pm 100$K, but not if the temperature range is expanded to temperatures of $T < T_g - 100$ K. One example of this is shown in FIG. 4.

The measured values are shown as hollow circles. Curve 1 shows a fit of the thermal displacement function according to equation (9), wherein $T = T_f$ was set. Curves 2, 3, and 4 were calculated by a fit to the measured values using a model of the invention according to equations (18) to (22). Specifically therein, the thermal displacement function of this model is given by the exponential factor in equation (21).

Curve 1 shows good agreement with the measured values at temperatures above $T_g$, but below this glass transition temperature the curve quickly deviates from the measured values. The model according to equations (18) to (22) found for the room temperature range reveals good results between −50° C. and +80° C. (curve 4). Curves 2 and 3 were also calculated using the model of the invention and were fitted to the measured thermal displacement function for temperature ranges between temperatures around $T_g$ (curve 2) and around 300° C. (curve 3).

A striking difference between the two temperature ranges for curves 2 and 3 is the slope of the curve "displacement function as a function of temperature" or equivalently the model parameter B of activation energy. For example, for a specific glass it has a value of $B(T_g)=27000$ K for temperatures around $T_g$, and of $B(T_g)=4500$ K at temperatures around room temperature for the same glass.

For a viable prediction modeling it is desirable, that the mathematical model describes both the temperature range around glass transition and the temperature range around room temperature in sufficiently precise manner and with the same model parameters.

Below, one embodiment of the invention will be described, in which time-delayed deformations of a glass or a glass ceramic may be determined and predicted for a wide temperature range using a suitable displacement function.

Surprisingly it has been found that no fundamentally new model is needed for the large temperature range. A significant difference between the known equations and this invention, however, is that the real temperature T in the model approaches of the displacement function according to equations (8) to (11) is replaced by a weighted sum $(1-q)\cdot 1+q\cdot T_f$ of the real temperature and the fictive temperature. According to yet another embodiment of the invention, the real temperature is replaced by an exponential weighted product $T^{(1-q)}\cdot T_f^q$ of the real temperature and fictive temperature $T_f$. In both cases, the so modified thermal displacement functions result in a significantly better match between measurement and model, in particular even if the fitting range of the model ranges from high temperatures of $T_g<T$ to low temperatures of $T<T_g-100$ K.

Therefore, in addition to model parameters B and C, a third model parameter q has to be determined, in the limits of $0<q<1$. This results in the following logarithms of displacement functions, $\log(a_T)$, which are particularly suitable for the invention:

$$\frac{B}{((1-q)\cdot T + q\cdot T_f)(1 - C/T_f)} - \frac{B}{T_{ref} - C}; \quad (23)$$

$$\frac{B}{(1-q)\cdot T + q\cdot T_f}\exp\left\{\frac{C}{T_f}\right\} - \frac{B}{T_{ref}}\exp\left\{\frac{C}{T_{ref}}\right\}; \quad (24)$$

$$\left(\frac{B}{(1-q)\cdot T + q\cdot T_f}\right)^c - \left(\frac{B}{T_{ref}}\right)^c; \quad (25)$$

$$\frac{B}{T^{1-q}T_f^q(1 - C/T_f)} - \frac{B}{T_{ref} - C}; \quad (26)$$

$$\frac{B}{T^{1-q}T_f^q}\exp\left\{\frac{C}{T_f}\right\} - \frac{B}{T_{ref}}\exp\left\{\frac{C}{T_{ref}}\right\}; \quad (27)$$

$$\left(\frac{B}{T^{1-q}T_f^q}\right)^c - \left(\frac{B}{T_{ref}}\right)^c; \quad (28)$$

$$\frac{B}{T_f - C} - \frac{B}{T_{ref} - C}; \quad (29)$$

$$\frac{B}{T_f}\exp\left\{\frac{C}{T_f}\right\} - \frac{B}{T_{ref}}\exp\left\{\frac{C}{T_{ref}}\right\}; \quad (30)$$

$$\frac{B}{T_f}\exp\left\{\frac{C}{T_f}\right\} - \frac{B}{T_{ref}}\exp\left\{\frac{C}{T_{ref}}\right\}; \quad (31)$$

$$\left(\frac{B}{T_f}\right)^c - \left(\frac{B}{T_{ref}}\right)^c. \quad (32)$$

A particularly robust model results when the model with q=1 and the measurements match sufficiently, because in that case the third model parameter q is fixed in effect and has no uncertainty per definition. This applies to the last four terms (29)-(32). Therefore, such a model fit is preferable. However, it does not succeed for every material.

Therefore, in one further embodiment of the invention, a thermal displacement function with model parameters B, C, q is determined based on the measured values of time-varying deformation, with a thermal displacement function with a logarithm selected according to any of expressions (23) through (32), wherein $T_{ref}$ denotes a fixed selected reference temperature and $T_f$ denotes the fictive temperature of the glass or glass ceramic material. From the fitted thermal displacement function, a time-dependent deformation of the glass or glass ceramic material under the effect of a temperature change or a time-varying mechanical stress may then be determined again. Preferably, when doing so, one of terms (29) to (32) or a corresponding displacement function is selected.

In addition to model parameters B and C of the displacement function, one or more weighting factors $w_k$ and time constants $\tau_{k,ref}$ may then be fitted to the measured values, wherein expression (7) mentioned above applies to the relaxation times $\tau_{k}$.

Figure 5:
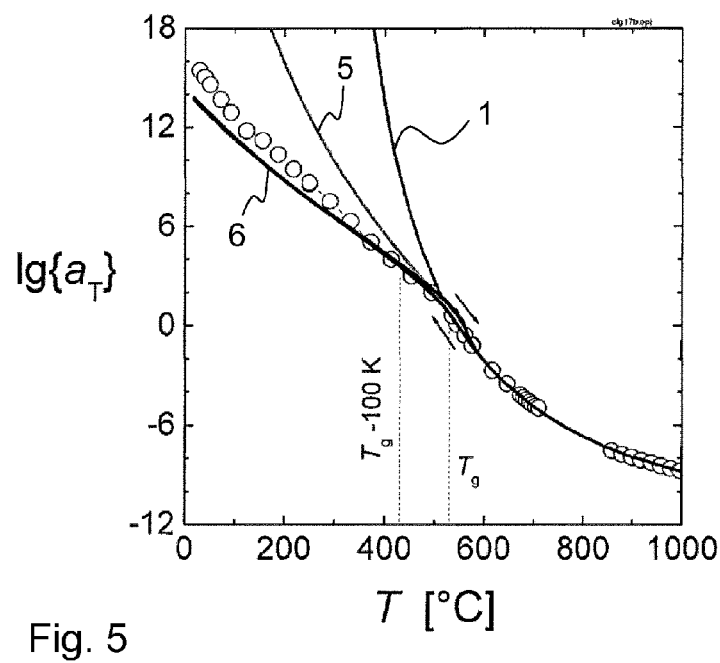

For this purpose, FIG. 5 again shows the measured values of the thermal displacement function and the displacement function according to equation (9), with $T=T_f$ (curve 1). Additionally shown is the displacement function according to equation (9) with a fictive temperature calculated according to (1)-(7) (curve 5). Finally, curve 6 is a displacement function of the invention according the above terms (23) to (32) fitted to the measured values. Specifically, term (27) was selected as a logarithm of the displacement function, and parameter q was set to a value of 0.32. As is apparent from curve 6, the calculated thermal displacement function matches very well with the measured values across the entire temperature range from room temperature to the softening point.

According to a yet another embodiment of the invention, a particularly suitable displacement function may be obtained by combining the displacement functions according to equations (8) and (23) through (32). For this purpose, a displacement function $a_T$ according to the following equation is used:

$$a_T = \frac{1}{\sum_{\Phi=A,B,C,...} \frac{1}{a_{T,\Phi}}} \quad (33)$$

In this equation, the index $\Phi=A, B, C, \ldots$ serially numbers the displacement functions according to equations (8) and (23) through (32). Accordingly, $a_{T,A}$ is the displacement function according to equation (8), $a_{T,A}$ is the displacement function according to equation (23), $a_{T,C}$ is the displacement function according to equation (24), and so on. The displacement function according to equation (33), although being computationally intensive, is especially preferred since this function is able to represent the limitation of two or more relaxation processes A, B, C, ... underlying equations (8), (23) through (32).

The measuring method for measuring the structural relaxation used to determine the relaxation times and model parameters will now be described in more detail by means of examples.

According to one embodiment of the invention, a time-dependent measurement of thermal expansion is performed in a temperature range in which the relaxation generates significant contributions to the property to be evaluated, and into which the application temperature range of interest falls. Preferable used for the at least two times of time-dependent measurement of the deformation of the glass or glass ceramic material at different rates of change in temperature or mechanical stress is a temperature range within a temperature interval from −70° C. to +100° C., or from −50° C. to +150° C. For the exemplary ZERODUR glass ceramic, a temperature range between −10° C. and +50° C. was selected, because above 50° C. relaxation is very fast.

Also, until −10° C. the measurement effort is low, and the temperature interval covers the main application temperatures. For determining the relaxation parameters, both isothermal temperature levels and non-isothermal temperature programs (with specified heating and cooling rates) can be used.

For measuring thermal expansion, a pushrod dilatometer designed for the temperature range mentioned above was used, with a measurement accuracy of better than 6.2 ppb/K and a reproducibility of 1.2 ppb/K.

Figure 6:
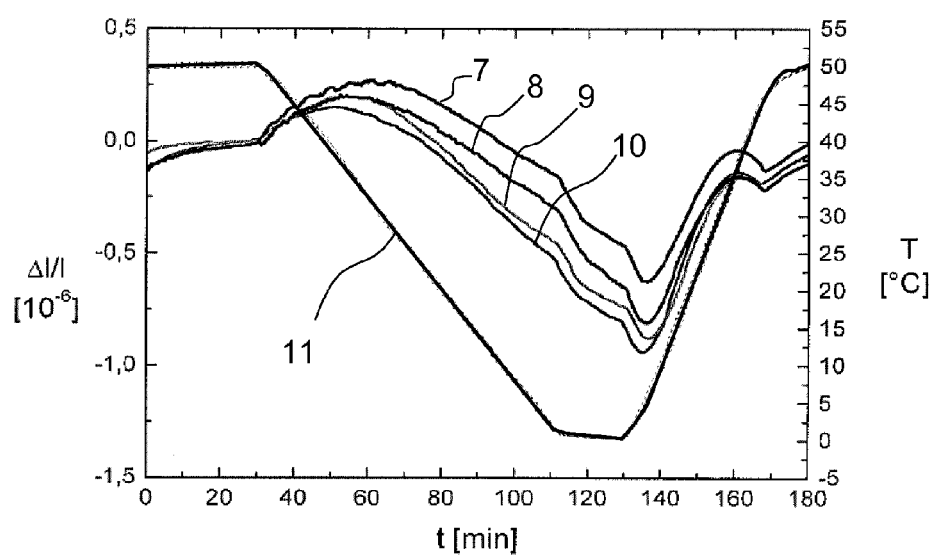
FIG. 6 shows a measurement of relaxation spectra of four different samples.

FIG. 6 shows measurements of thermal expansion from which the relaxation spectra and the corresponding relaxation times of four glass ceramic samples are determined, wherein the relative thermal expansion $\Delta l/l$ was measured using a non-isothermal temperature-time profile. Despite the fact that all the samples were ZERODUR glass ceramics, i.e. all samples were made of the same type of glass ceramics, the samples exhibit variations in their relaxation behavior and therefore also in the individual relaxation times. The individual curves of the four samples are denoted by reference numerals 7, 8, 9, 10. Reference numeral 11 designates the temperature profile. As can be seen from the temperature profile, the temperature was varied between 0° C. and 50° C., with different rates of change in temperature during temperature reduction and the subsequent temperature increase.

According to another embodiment of the invention, an isothermal stepped temperature profile is applied. The relaxation spectra are determined at the individual temperatures, by altering the temperature starting from a state of equilibrium and then evaluating the relaxation curve. Typically, the change in temperature is a few Kelvin, preferably not more than 10 Kelvin.

Figure 7:
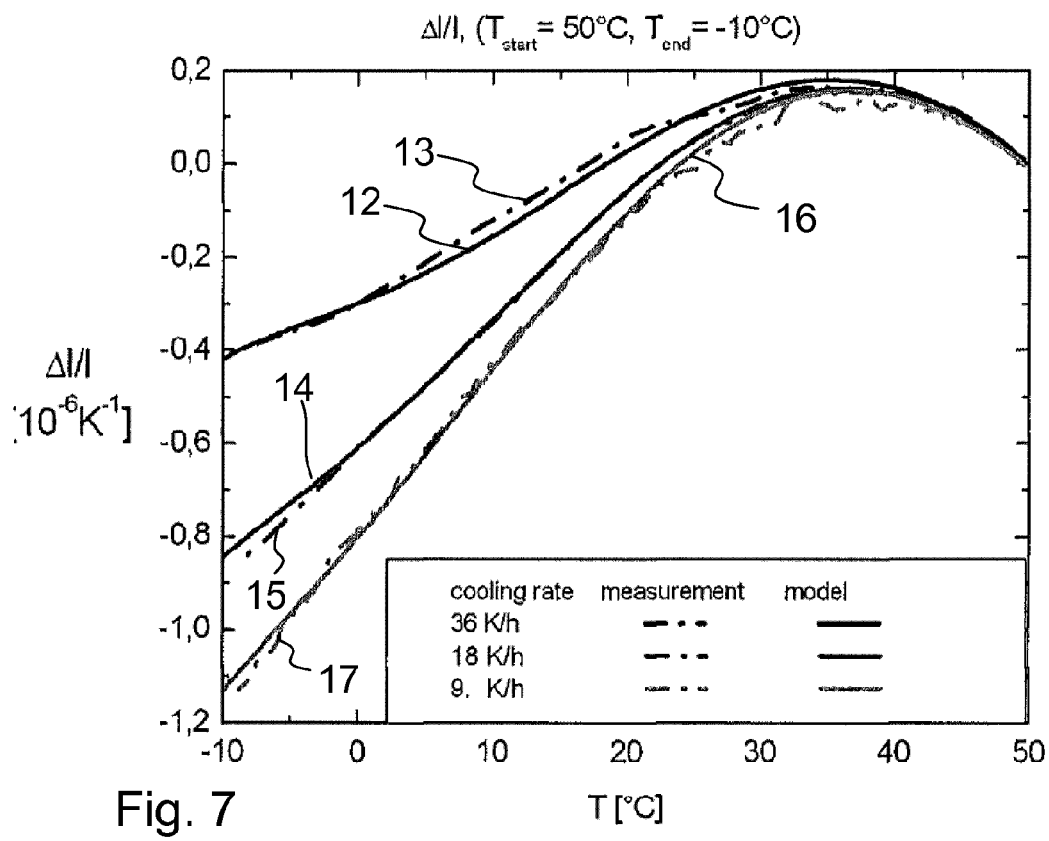
FIG. 7 shows the thermal expansion of a sample at different cooling rates.

According to one embodiment of the invention, the material parameters or model parameters including the relaxation times are determined by applying a simulation model with a numerical optimization algorithm. Suitable algorithms are, for example, the Levenberg-Marquardt algorithm, or the Gauss-Newton algorithm. These algorithms fit the model parameters so that the differences between model prediction and measurements are reduced to a minimum. For this purpose, one temperature measuring program can be used for fitting, as shown in FIG. 6, or several different measuring programs, as shown in FIG. 7. FIG. 7 shows the time-dependent change in length for a single sample at different cooling rates, and the respective calculated time-dependent change in length. In the illustrated example, cooling rates of 36 Kelvin per hour (curves 12, 13), 18 Kelvin per hour (curves 14, 15), and 9 Kelvin per hour (curves 16, 17) were employed. Curves 12, 14, 16 shown by solid lines represent the calculated changes in length, curves 13, 15, 17 shown in dotted lines represent the measured changes in length.

Figure 8:
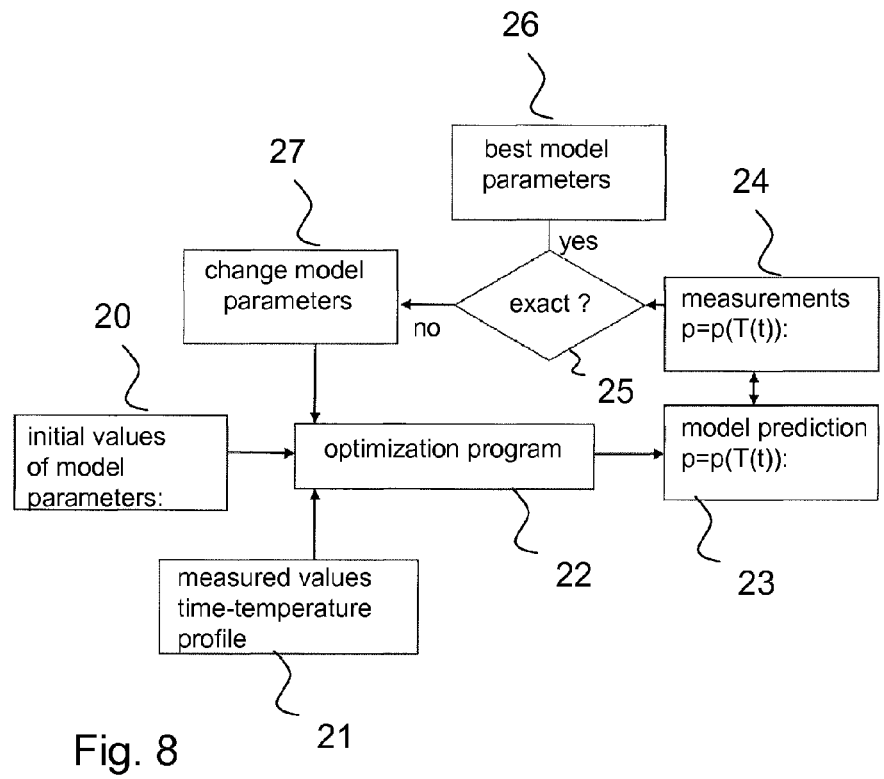
FIG. 8 is a flow chart of an optimization program for determining model parameters of thermal expansion.

FIG. 8 shows an exemplary embodiment of an optimization program for determining the model parameters according to the model of equations (17)-(22) in combination with a thermal displacement function according to any of terms (21.2) and (23) through (32).

The program starts with initial values of model parameters, step 20, and with the measured values of the temperature-time profile, step 21. These parameters are supplied to an optimization program 22, which calculates a model prediction of a thermo-mechanical parameter p which is dependent of time and temperature. For example, this parameter may be the relative elongation $\Delta l/l$, such as detected in the measurements illustrated in FIGS. 3, 6 and 7. Optimization program 22 compares the model prediction 23 with the measurements 24 and decides (decision 25), whether an optimized set of model parameters is already existing or not. When an optimized set has been found, for example, when the deviation of calculated parameter p from the measured parameter is below a threshold, the optimization program outputs the model parameters, in step 26. Otherwise, the model parameters are changed, step 27, and another model prediction for parameter p is calculated with the modified model parameters, in step 23.

Figure 9:
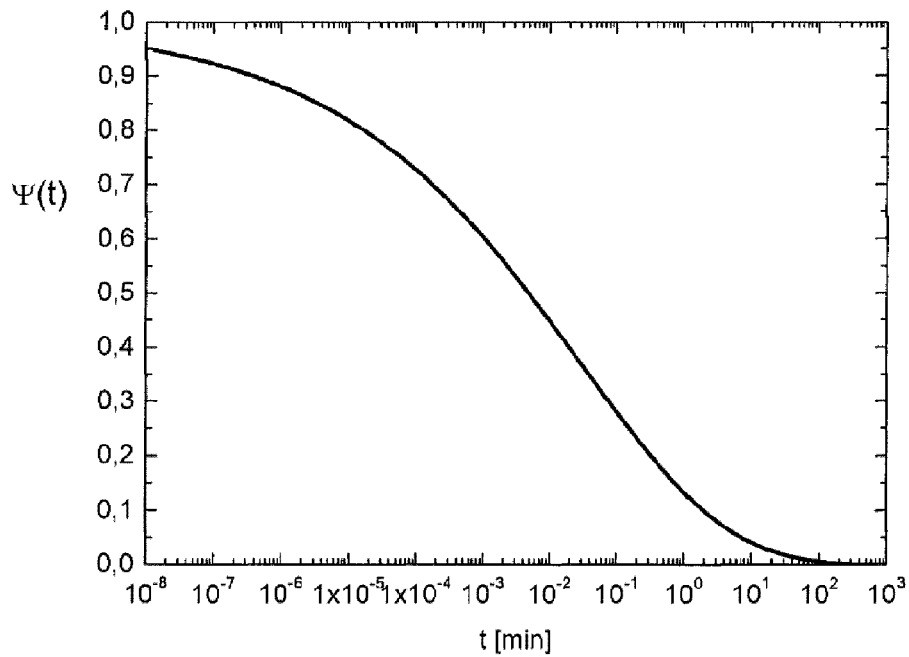
FIG. 9 shows a typical relaxation function for a reference temperature, reflecting the relaxation spectrum.

From the model parameters, the relaxation function according to equation (5) may be calculated. FIG. 9 shows a typical relaxation function $\Psi(t)$ of a fitted set of model parameters for a specific reference temperature as a function of the time t of relaxation.

According to one embodiment of the invention, first model parameters are determined based on a measurement of time-dependent deformation, for example as described with reference to FIGS. 6 to 9, and these model parameters are then verified in a cyclic measurement of deformation, in which the temperature or mechanical stress is cyclically altered repeatedly. This cyclic measurement may in particular be one of the at least two measurements of time-dependent deformation with different rates of change in temperature or a mechanical stress.

For verifying the determined model parameters including the relaxation times, it is advantageous if the temperature-time profile in the cyclic measurement or the change of mechanical stress is substantially different from the temperature-time profiles used to determine the model parameters.

Figure 10:
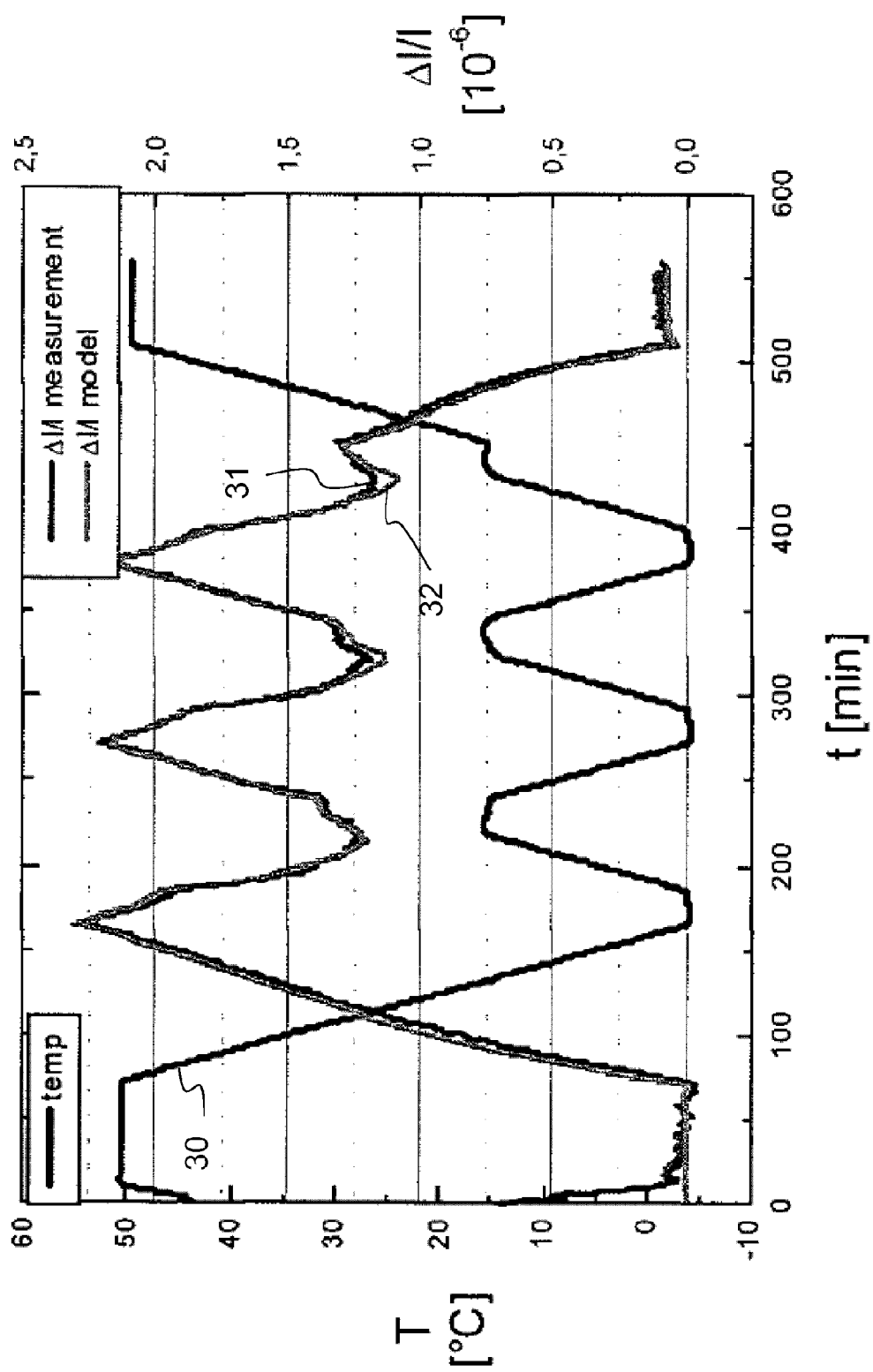
FIG. 10 shows a measurement of thermal expansion of a glass ceramic under a cyclic temporal change in temperature, and a calculated thermal expansion for comparison.

FIG. 10 shows such a cyclic measurement, and, for comparison, also shows the profile calculated based on the relaxation times and other model parameters. The sample was cyclically heated and cooled, and relative expansion $\Delta l/l$ was measured and calculated. The rate of change of the temperature ramps was about 0.6 Kelvin per minute. In FIG. 10, curve 30 denotes the temperature profile, curve 31 denotes the thermal expansion as measured, and curve 32 the thermal expansion as calculated. As can be seen from the nearly perfect match of the expansions as calculated and as measured, the invention permits to very accurately predict the time-temperature behavior of thermal expansion of glass ceramics.

Generally, without limitation to the exemplary embodiment shown, the temporal course of thermal expansion and/or a thermal expansion of the glass or the glass ceramic at a specified time can now be calculated based on the determined relaxation times and weighting factors for a specified temperature-time profile.

Thus, a method is provided for predicting thermal expansion taking into account the thermal history and thermal conditions of use and the associated relaxation phenomena. Once the material parameters are known, the relaxation model may be used for simulation and prediction of relaxation phenomena of glasses and glass ceramics under real operating conditions. The user is provided with a significantly increased accuracy of material properties.

Figure 11:
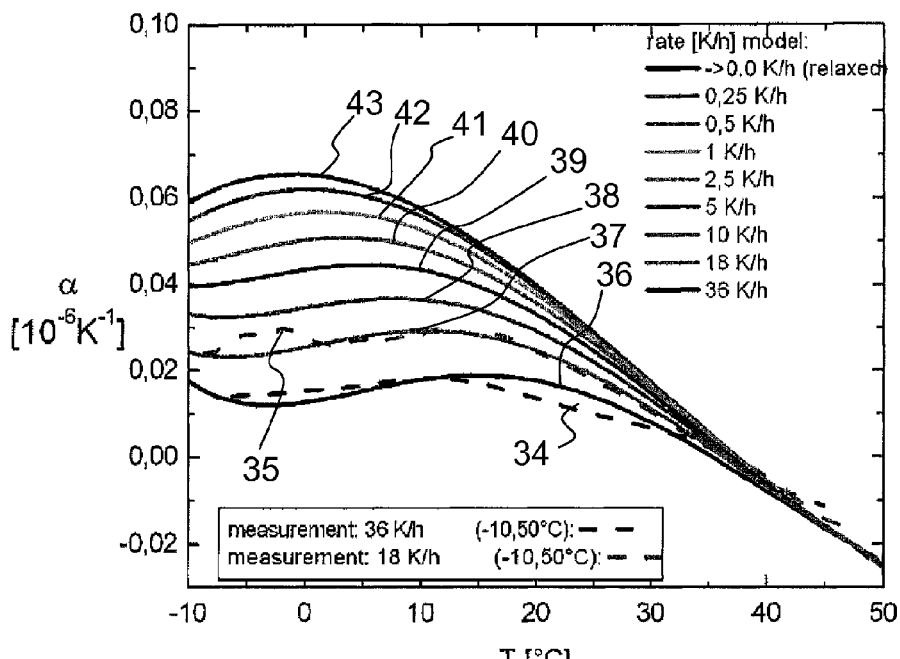
FIG. 11 shows the coefficient of thermal expansion as a function of different rates of change in temperature.

This allows to determine the material properties for the quasi-static case and the intermediate stages until then. This also includes the so-called long-term shrinkage of glass ceramics. An example is illustrated in FIG. 11. This graph shows the linear coefficient of thermal expansion, or thermal expansion coefficient, of a glass ceramic as a function of different rates of change in temperature and for a temperature range between −10° C. and +50° C. Curve 34 represents a measurement at a rate of change of 36 K/h (Kelvin per hour), and curve 35 represents a measurement at a rate of change of 18 K/h. Curves 36 and 37 represent the calculated coefficients of thermal expansion at these rates of change, i.e. at 36 K/h and 18 K/h. Here, again, a very good agreement with the measurement is apparent. Curves 38 through 43 represent further calculated thermal expansion coefficients for rates of change of 10 K/h (curve 38), 5 K/h (curve 39), 2.5 K/h (curve 40), 1 K/h (curve 41), 0.5 K/h (curve 42), 0.25 K/h (curve 43), and for the quasi-static case with a rate of change near 0 K/h (curve 43).

According to one embodiment of the invention, therefore, without being limited to the specific example shown in FIG. 11, the coefficient of thermal expansion (CTE) of the glass or glass ceramic material is determined based on a rate of change in temperature.

In this manner, the expansions to be expected in an application cycle can be calculated with increased accuracy. By using the invention, the corrections in shape, such as in telescope mirrors, which are necessary for compensating thermal expansions can be better calculated.

For example, especially batches of material with supposedly inferior properties according to standard measurements, may exhibit the better performance in a specific application. Examples of this will now be explained with reference to FIGS. 12 through 15.

The examples have in common, that a profile of temperature or a mechanical stress is predefined, the deformation under the effect of the predefined profile is calculated as a function of time for a plurality of glasses or glass ceramics, and based on this calculation, that glass or glass ceramic material is chosen, which exhibits the smallest deformation among the plurality of these glass or glass ceramic materials. The calculation of deformation in turn typically requires that a deformation of a glass or glass ceramic material is measured at least twice as a function of time with different rates of change in temperature or a mechanical stress as described above, in order to determine the model parameters, including the relaxation times of the material. Instead of selecting the best material in this manner from a number of available glass or glass ceramic materials, it is also possible to predefine a limit value of deformation under specific application conditions, and then to check using the invention whether one or more of these materials meet this limit value, whereupon this material or these materials will be selected for the particular application. In this case, therefore, a glass or glass ceramic article exhibiting a predefined time-delayed thermal or mechanical deformation is provided by predefining an allowable range of values of a time-delayed thermal or mechanical deformation in a temperature range having an upper limit of not higher than 100 K below the glass transition temperature;

measuring a deformation of the glass or glass ceramic material at least twice as a function of time and with different rates of change in temperature or a mechanical stress; wherein the measurements are performed at temperatures of not higher than 100 K below the glass transition temperature, and wherein based on these measurements, a plurality of relaxation times of the glass or glass ceramic material are determined for a reference temperature, and weighting factors are determined, which represent a weight of the relaxation times in the relaxation of the glass or the glass ceramic, and wherein based on the relaxation times and weighting factors, a time-delayed change of a temperature-dependent or stress-dependent time-delayed deformation is calculated as a function of a predefined temperature change or stress change.

The thermal or mechanical deformation is extrapolated to the predefined allowable range of values using the one or more relaxation time(s) and weighting factors, in particular using equation (17), and it is compared whether the extrapolated thermal or mechanical deformation is within the range of values. Subsequently, the glass or glass ceramic material is chosen when the extrapolated value of the time-dependent thermal or mechanical deformation is within the allowable range of values.

Figure 12:
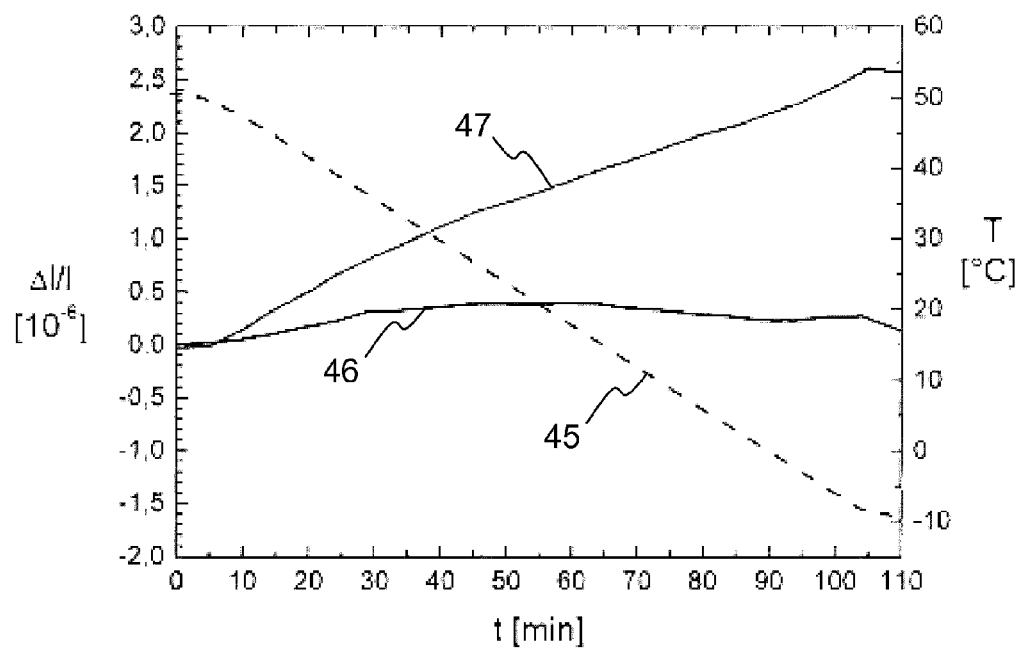
FIG. 12 shows measured values of thermal expansion of two glass ceramic samples.

FIG. 12 shows measured values of time-dependent thermal expansion of two glass ceramic samples from two different production batches. Curve 45 denotes the temperature profile (cooling from +50° C. to −10° C. within 110 minutes). Curve 46 represents the time-dependent thermal expansion of the first sample as measured, curve 47 the time-dependent thermal expansion of the second sample. According to this laboratory measurement, the glass ceramic batch from which sample 1 was taken appears to have substantially better properties in terms of a lowest possible thermal expansion, since across the entire temperature range the change in length is significantly smaller than that of sample 2, curve 47.

Figure 13:
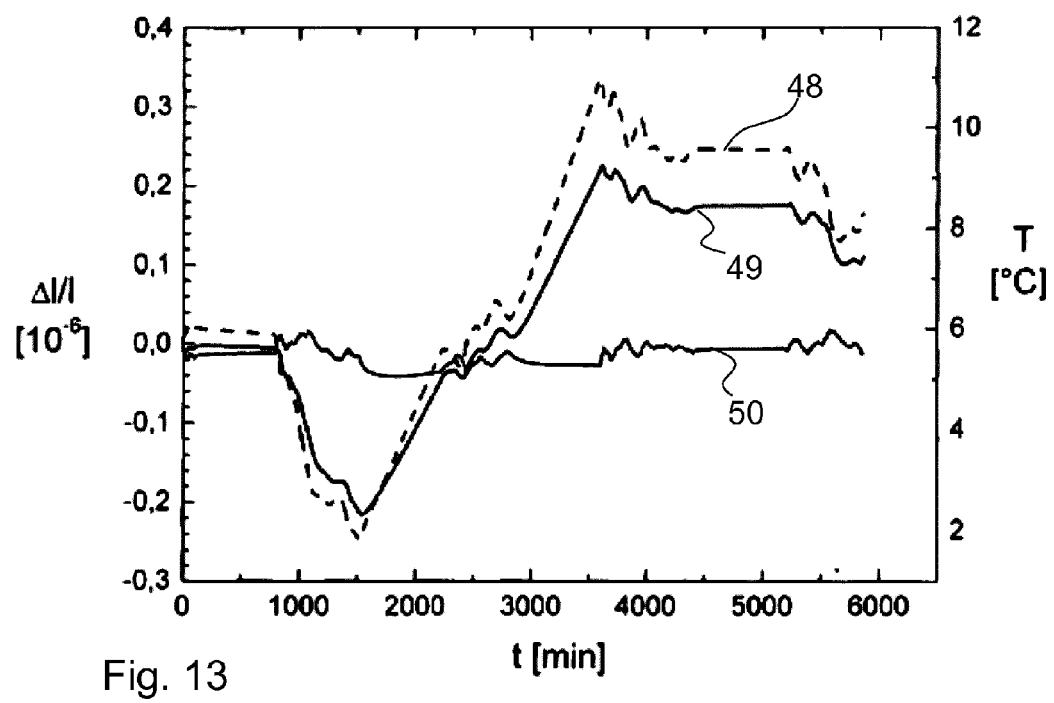
FIG. 13 shows thermal expansion of the two samples when subjected to a specific temperature-time profile.

FIG. 13 shows the thermal expansion of the two samples as calculated according to the invention under the effect of a specific temperature-time profile (curve 48) as it may occur in operation. The time scale herein is much greater, and the interval of temperature change of less than 10° C. is substantially smaller than in the laboratory measurement shown in FIG. 12. Therefore, the rate of change in temperature is also much smaller. Curve 49 represents the thermal expansion of sample 1, curve 50 the thermal expansion of sample 2. From this calculation it is now apparent that under the specified conditions sample 2 exhibits a lower thermal expansion over a long period of time. For an application with temperature profiles as in the exemplary embodiment it is therefore advantageous to use the glass ceramic of the second batch and to produce a glass ceramic component therefrom, although the thermo-mechanical properties thereof appear to be inferior at first glance.

Figure 14:
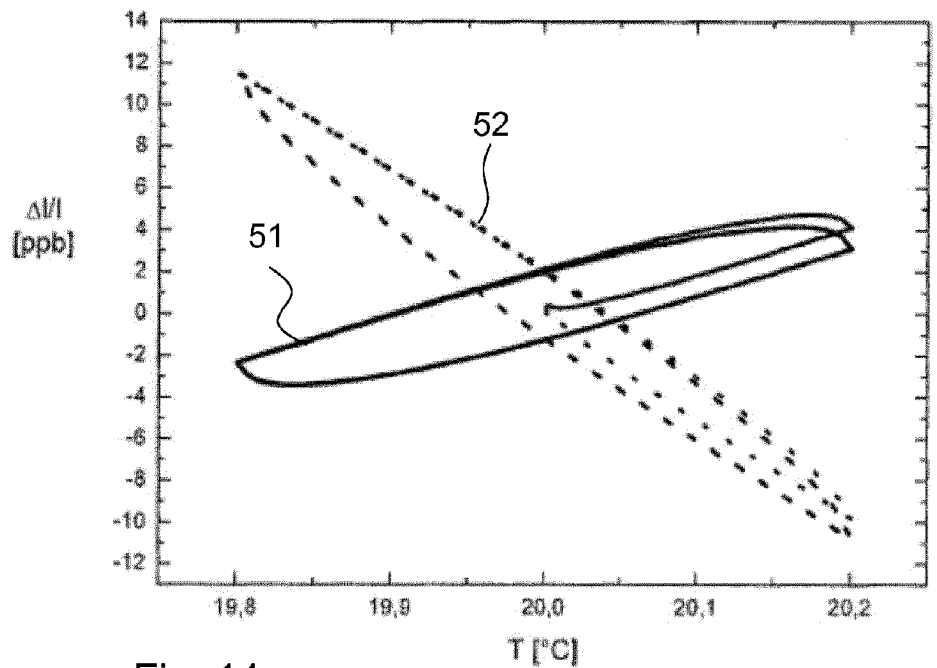
FIG. 14 shows a prediction of thermal expansion of glass ceramic components of a coordinate measuring device.

FIG. 14 shows, as another example, the thermal expansion of two glass ceramic components of a coordinate measuring device under the thermal conditions occurring in this application. The components are identical except for the batch of glass ceramic material. Here, the maximum thermal expansion according to curve 51 which was calculated based on the relevant model parameters as measured, is smaller than that of curve 52. Accordingly, it will be better to select the component for which curve 51 was calculated for the coordinate measuring device.

Figure 15:
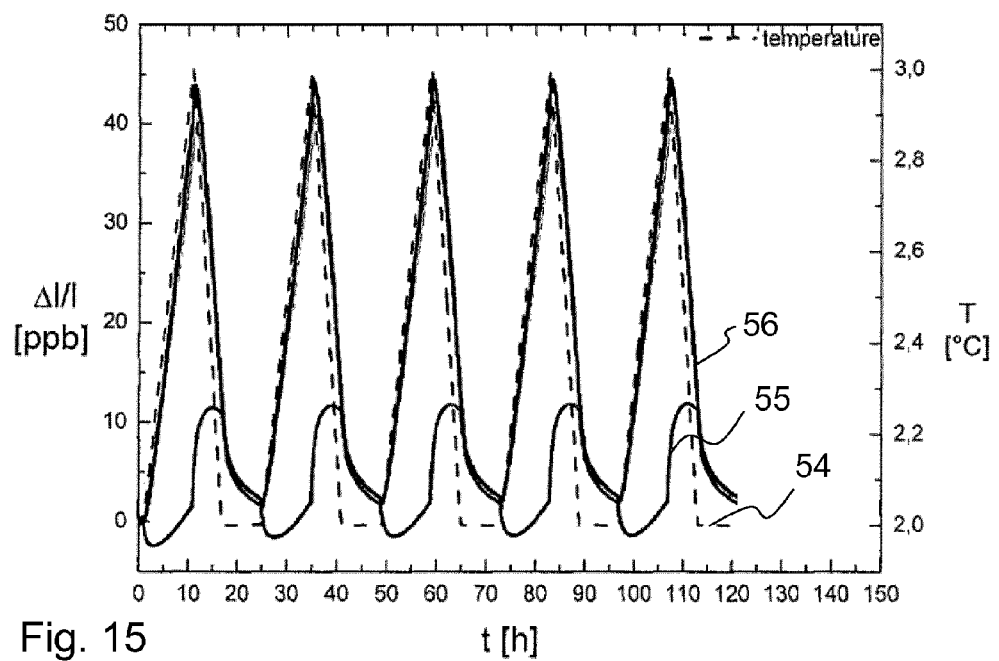
FIG. 15 shows a prediction of thermal expansion of two samples for a glass ceramic telescope mirror.
Figure 16A:
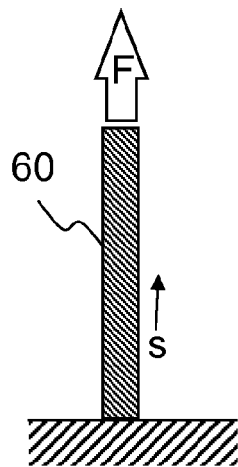
Figure 16B:
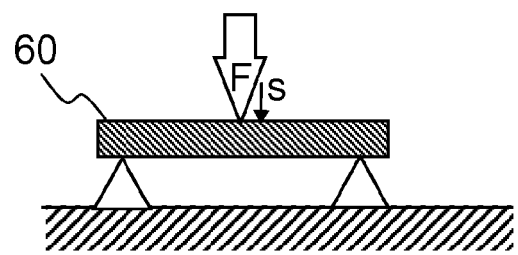
Figure 16C:
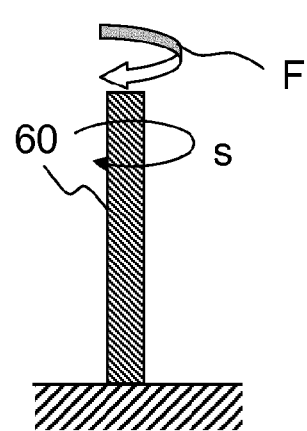
Figure 16D:
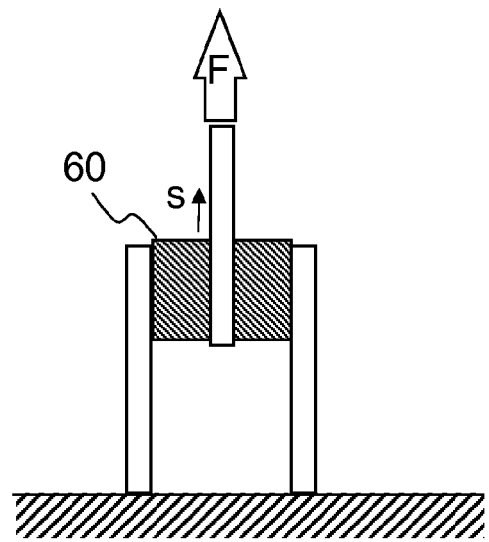

FIG. 15 shows a prediction of thermal expansion in telescope mirrors made of material from three glass ceramic batches, whose model parameters were determined based on a measurement of relaxation times. Here, the temperature (curve 54) varies depending on the time of day, albeit slightly. The time-dependent thermal expansion of two out of the considered samples is virtually identical (curve 56) under these application conditions. For the batch for which curve 55 was calculated, in contrast, a different time-dependent expansion in length results (curve 55), and this with a substantially lower maximum value. Therefore, advantageously, the glass ceramic of curve 55 will be selected for this application, and the telescope mirror will be produced therefrom.

In addition to a careful selection of glass or glass ceramic components already produced, the model prediction also enables to selectively manufacture materials in a manner so as to comply with the specific application conditions, as already explained before in the introductory part. For this purpose, in manufacturing the composition and/or temperature-time profile during ceramization may be predetermined by interpolation or extrapolation of the properties of these already existing glasses or glass ceramics.

Another application of the invention is the prediction of delayed elasticity of glasses and glass ceramics under mechanical stress, also with varying temperature. This prediction may be used upon material removal under mechanical stress, in particular in stress polishing of high-precision components, especially high-precision optical components. Stress polishing is employed to produce aspherical surfaces. This technique is used for both glasses and glass ceramics. A well-known application is the stress mirror polishing of telescope mirrors. Typically in this case, the reflecting body is subjected to mechanical stress, and then a spherical surface is ground into it. During subsequent relaxation of the mirror body and the resulting re-deformation, the spherical surface will deform into a paraboloid segment. However, the delayed elasticity of glass or glass ceramic materials inter alia leads to a time-delayed deformation of the surface to be treated during material removal. Ultimately this will result in a deviation in shape of the polished optical surface from the intended optimal shape.

One embodiment of the invention in form of a method for predicting delayed elasticity will now be described hereinafter. Here, again, the invention enables to predict delayed elasticity for temperatures below the glass transition, i.e. for $T<T_g-100$ K taking into account the thermo-mechanical history and freely selectable thermo-mechanical conditions of use and the associated relaxation phenomena.

What is determined are weighting factors $w_k$ (according to equation 13) and relaxation times $\tau_{ref,k}$ (equation (13) in combination with equation (7)) for the bulk modulus and the shear modulus. For the shear modulus, or for properties from which the shear modulus can be deduced, more or less widely used measurement methods are known. Several configurations for measuring a shear modulus are shown in FIGS. 16A to 16D. The glass or glass ceramic sample is designated by reference numeral 60 in each case. F is the force acting on the sample, s designates the direction of the measured deformation. The measurement may be performed under uniaxial drawing (FIG. 16A), or under deflection (FIG. 16B), or under a torsional (FIG. 16C), or shearing (FIG. 16D) force. The mechanical stress may be applied quasi-statically after impulsive loading, or dynamically, isothermally, or with a change in temperature. The measuring methods differ in complexity and accuracy. For the same accuracy requirements, the bulk modulus is generally more difficulty measured, or even hardly. But it may be calculated from the difference between Young's modulus and shear modulus.

What is measured therefore is the deformation of the sample as a function of time and mechanical stress for a predetermined constant or variable temperature. For this purpose, the deformation is measured at least twice as a function of time and at different rates of change of the mechanical load. One of these measurements may be used to verify the model parameters which had been determined based on at least one previous measurement.

Since the time-dependent deformation of the sample is low when compared to the total sample deformation, it is especially advantageous to ensure a sufficiently high sensitivity and reproducibility of the measurement method. A fit of the mathematical model using equations (12) through (22) and an associated displacement function according to any of terms (23) through (32) will provide the model parameters. The fit may again be accomplished using an optimization program as described with reference to FIG. 8.

Then, by using the model parameters and the model, calculations of component deformation under specified stress histories upon material removal under mechanical stress may be performed, for example for a mirror blank, in particular for stress mirror polishing and with specified temperature histories.

For example, FIG. 17 shows an exemplary time profile of a deflection moment acting on the outer circumference for bowl-shaped deformation of a mirror segment.

Furthermore, FIG. 18 shows the maximum bowl-shaped deflection $s_{pv}$ as measured and as calculated, as a function of time. The timeline herein starts after time $t_5$ as depicted in FIG. 17, i.e. after the component has been relieved. What is found due to delayed elasticity is a deflection of the component arising and increasing only after the mechanical stress. This deflection also depends on the duration of the mechanical stress, i.e. the period between times $t_2$ and $t_3$ in the example shown in FIG. 17.

In FIG. 18, curves 62 and 63 represent the maximum bowl-shaped deflection as measured and as calculated, for a duration $t_3-t_2$ of 3 hours. Curves 64 and 65 represent the maximum bowl-shaped deflection as measured and as calculated for a duration $t_3-t_2$ of 90.5 hours.

Generally, this exemplary embodiment is based on the fact that the deformation of a glass or glass ceramic material is measured at least twice, as a function of time and with a time-varying mechanical stress, that based on the these measurements relaxation times for the model are determined, and that based on the model a deformation of a component is calculated as a function of a time-varying mechanical stress.

Specifically, this permits to calculate a deflection, in particular a bowl-shaped deflection of an optical component, such as specifically that of a telescope mirror following stress mirror polishing, inter alia. In particular, this pre-calculated deflection may be taken into account when polishing the component and so may be compensated for.

Generally, the model is applicable to almost any period of time. Therefore, the method of the invention may be used to model and predict long-term expansions within an observation period from 1 year to 40 years. This allows for an evaluation of long-term stability and change of length scales. Generally, therefore, a deformation of the component may be predetermined for a time between 1 year and about 40 years in the future. The invention is likewise suitable for predicting the deformation for nearer points in time, in particular for longer prediction periods of a duration of preferably at least 100 minutes, as can also be seen from the attached figures.

For this purpose, in one embodiment of the invention, the thermal displacement function $a_T$ is expressed using viscosity t, as follows:

$$a_T = \frac{\eta}{\eta_{ref}}, \quad (34)$$

wherein $\eta_{ref}$ is a reference viscosity.

FIG. 19 shows the viscosity profile of several reference samples, wherein the values were determined by measuring the thermal expansion of these samples. The range covered by these values ranges from several hours to one day.

Now, to be able to describe the relaxation process at room temperature for times ranging from minutes to years, the displacement function has to be known for this entire time period. Therefore, the viscosity profile of FIG. 19 has to be extended towards both lower and higher temperatures. Viscosities clearly exceeding a value of $10^{13}$ dPa·s are virtually not measurable using conventional viscosity measurements, due to the necessary long measurement times.

However, it is known that different material properties obey the same displacement function (Jakobson, B., Hecksher, T., Christiansen, T., Olsen, N. B., Dyre, J. C., Niss, K., "Identical temperature dependence of the time scales of several linear-response functions of two glass forming liquids", J. Chem. Phys., Vol. 136, 081102 (2012)). Against this background, the viscosity curve of FIG. 19 may be extended by measuring the permittivity and the internal mechanical friction of the glass or glass ceramic article. At higher temperatures, the viscosity is determined using deflection tests.

FIG. 20 shows the profile of the viscosity curve extended in this way.

Based on these viscosity values, the course of the displacement function is then also given for all relevant temperature profiles.

Therefore, according to one embodiment of the invention, without limitation to the exemplary embodiments, it is suggested for the thermal displacement function to be expressed as a ratio of viscosity η to a reference viscosity, or to be calculated from this ratio. In this case, the viscosity may be determined by measuring at least one of quantities permittivity and internal mechanical friction of the glass or glass ceramic article, and/or by deflection tests on the glass or glass ceramic article. Preferably, the measurements of permittivity, internal mechanical friction and the deflection tests are combined, such as shown in FIG. 20, for example.

Now, the application of this embodiment of the invention to the Thirty Meter Telescope (TMT) project on Mauna Kea in Hawaii will be described. The operating temperature of this telescope was specified to between −5° C. and +9° C., with a temperature gradient around 0.7° C./h (integrated over 60 minutes).

With reference now to FIG. 21, the results of the studies for this telescope project will be explained. Curve 71 in FIG. 21 shows the temperature profile as measured on Mauna Kea between Mar. 8 and 11, 2008. This profile has been smoothed to reduce noise. Furthermore, the temperature profile was linearized between the temperatures in the morning and those in the evening. This is based on the assumption that the telescope will be exposed to the influences of an air conditioner during the day, with the dome closed, so that the telescope is at the temperature prevailing outside the dome at the beginning of the night.

The average nocturnal temperature on Mauna Kea during the measurement period was 2° C., with a minimum at −0.38° C. and a maximum at 5° C.

Curves 72 and 73 represent the thermal expansion of two samples. While curve 72 of the first sample reveals a total thermal expansion of about 0.2 ppm, this value is only about 0.1 ppm for the second sample (curve 73). This means that the second material is more suitable to be used as a material for the telescope mirror.

FIG. 22 shows results of measurements of thermal expansion for different material samples N, O, and T. In terms of their "thermal history", these samples were subjected to the conditions as set forth below, after all three samples had been ceramized in a similar manner first.

Samples T and O were subjected to an additional annealing following ceramization, during which they were again brought to the maximum ceramization temperature. During the subsequent cooling process, sample T was cooled to room temperature at −60 K/h, and sample O at −1 K/h. Sample N was not annealed again.

Due to these different pretreatments, the age of the three samples at the beginning of the measurements was:
Sample N: 992 days
Sample O: 125 days
Sample T: 119 days Finally, FIG. 23 shows a comparison of the experimental data of FIG. 22 with the calculated values.

The invention claimed is:

1. A method for determining time-delayed changes of temperature-dependent or stress-dependent physical quantities of a glass or a glass ceramic material, which depend on the relaxation state of the glass or glass ceramic, the method comprising:
   measuring a deformation of the glass or glass ceramic material at least twice with different rates of change in temperature and/or with a mechanical stress as a function of time, wherein the measurements are carried out at temperatures of not higher than 100 K below a glass transition temperature of the glass or glass ceramic material; and
   determining a plurality of relaxation times of the glass or glass ceramic material for a reference temperature;
   determining weighting factors, which represent a weight of the relaxation times in the relaxation of the glass or the glass ceramic material; and
   calculating a time-delayed change of a temperature-dependent or stress-dependent physical quantity as a function of a predefined temperature change or stress change based on the relaxation times and weighting factors.

2. The method as claimed in claim 1, further comprising:
   determining a fictive temperature of the glass or the glass ceramic material; and
   determining a time dependence of the fictive temperature.

3. The method as claimed in claim 1, wherein the measuring of deformation of the glass or glass ceramic material at least twice with different rates of change in temperature or mechanical stress as a function of time in a temperature range is performed within a temperature interval from −70° C. to +100° C.

4. The method as claimed in claim 1, further comprising:
   determining model parameters based on a measurement of time-dependent deformation; and
   verifying the model parameters by a cyclic measurement of deformation during which temperature or mechanical stress is cyclically changed repeatedly.

5. The method as claimed in claim 1, further comprising calculating, based on the relaxation times determined and assuming a predefined temperature-time profile, a temporal development of thermal expansion and/or a thermal expansion at a certain time.

6. The method as claimed in claim 1, further comprising determining a coefficient of thermal expansion (CTE) of the glass or glass ceramic material as a function of a rate of change in temperature.

7. The method as claimed in claim 1, further comprising:
   predefining a temperature profile or profile of mechanical stress;
   calculating a deformation under the effect of the predefined profile as a function of time for a plurality of glasses or glass ceramics; and
   choosing, based on the calculation, a glass or glass ceramic material among the plurality of the glass or glass ceramic materials that exhibits a smallest deformation.

8. The method as claimed in claim 1, further comprising determining a future deformation of the component for a time between 1 year and about 40 years in the future.

9. The method as claimed in claim 1, further comprising:
   measuring at least twice a deformation of a glass or glass ceramic material as a function of time under a mechanical stress varying over time;
   determining relaxation times based on these measurements; and
   calculating a deformation of a component as a function of a mechanical stress varying over time.

10. The method as claimed in claim 9, further comprising calculating a deflection of an optical component following a material removal under mechanical stress.

11. The method as claimed in claim 10, wherein the deflection previously calculated is accounted and compensated for during the material removal under mechanical stress.

12. The method as claimed in claim 1, wherein the step of calculating the time-delayed change comprises performing a calculation selected from the group consisting of calculating a change in length, calculating a change in volume, calculating a change in refractive index, calculating a change in heat capacity, calculating a change in shear modulus, calculating a change in bulk modulus, calculating a change in torsion modulus, and calculating a change in Young's modulus.

13. The method as claimed in claim 12, wherein a thermal displacement function is expressed as a ratio of viscosity $\eta$ to a reference viscosity, wherein the viscosity is determined by measuring permittivity and internal mechanical friction of the glass or glass ceramic article, and by deflection tests on the glass or glass ceramic article.

14. The method as claimed in claim 12, further comprising:
   determining relaxation times ($\tau_k$) at a reference temperature ($T_{ref}$), weighting factors ($w_k$), and parameters of a displacement function ($a_T$), a displacement function specifying how the relaxation of the glass or glass ceramic material changes as a function of temperature;
   determining therefrom state variables $T_{fA}$, $T_{fAi}$, where $T_{fA}$ is represented as a spectrum of the differently relaxing state variables $T_{fAi}$, by fitting the parameters of the following equations to the measured values:

(a) $\Delta p(T, T_{fA}) =$
$$p_s(T)\Delta T + p_f(T_{fA})\Delta T_{fA} = \sum_{i=0}^{n} p_{s,i}T^i\Delta T + \sum_{j=0}^{m} p_{f,j}T_{fA}^j\Delta T_{fA}$$

(b) $T_{fA} = \sum_{k=1}^{n} w_k T_{fAk}(t),$ (c) $\sum_{k}^{n} w_k = 1,$ (d) $\dfrac{dT_{f,A,k}}{dt} = \dfrac{T - T_{f,A,k}}{\tau_k},$ (e) $\tau_k(T) = \tau_k(T_{ref}) \cdot a_T,$ (f) $\Psi(t) = \sum_{k}^{n} w_k \cdot \exp\left[-\dfrac{t}{\tau_k}\right];$ wherein $p_s(T)$ is a specific change of physical quantity p per unit temperature, $\Delta T$, $\Delta T_{fA}$ is a change in temperature and fictive temperature, respectively, $p_f(T_{fA})$ is a time-delayed specific change of physical quantity p per unit temperature, $p_{s,i}$, $p_{f,j}$ are coefficients, and $\Psi(t)$ denotes a relaxation function; and subsequently determining, from these equations with known parameters, a time-dependent change of the physical quantity of the glass or glass ceramic material under the effect of a change in temperature or a mechanical stress varying over time.

15. The method as claimed in claim 14, further comprising determining the time-dependent change of the physical quantity at temperatures in a range from −50° C. to +80° C.

16. The method as claimed in claim 15, wherein the time-dependent change of the physical quantity comprises a deformation when subjected to a temperature or mechanical stress varying over time.

17. A method for providing a glass or glass ceramic article exhibiting a predefined time-delayed thermal or mechanical deformation, comprising the steps of:
   predefining an allowable range of values of a time-delayed thermal or mechanical deformation in a temperature range having an upper limit of not higher than 100 K below a glass transition temperature;
   measuring a deformation of the glass or glass ceramic material at least twice as a function of time with different rates of change in temperature or a mechanical stress, wherein the measurements are performed at temperatures of not higher than 100 K below the glass transition temperature, and wherein based on said measurements, a plurality of relaxation times of the glass or glass ceramic material are determined for a reference temperature, and weighting factors are determined, which represent a weight of the relaxation times in the relaxation of the glass or the glass ceramic, and wherein based on said relaxation times and weighting factors, a time-delayed change of a temperature-dependent or stress-dependent time-delayed deformation is calculated as a function of a predefined change in temperature or stress;

extrapolating the thermal or mechanical deformation to the predefined allowable range of values using the one or more relaxation time(s);

comparing whether the extrapolated thermal or mechanical deformation is within the range of values; and choosing the glass or glass ceramic material when the extrapolated value of time-dependent thermal or mechanical deformation is within the allowable range of values.

18. The method as claimed in claim 17, wherein providing the glass or glass ceramic article comprises manufacturing the glass or glass ceramic article for the predefined range of values, wherein the manufacturing conditions are adjusted in a manner so that the allowable range of values is achieved.

19. A glass or glass ceramic article exhibiting a predefined time-delayed thermal or mechanical deformation, the glass or glass ceramic material of said glass or glass ceramic article being selected by:

a predefined allowable range of values of a time-delayed thermal or mechanical deformation in a temperature range having an upper limit of not higher than 100 K below a glass transition temperature;

a measured deformation of the glass or glass ceramic material at least twice as a function of time with different rates of change in temperature or a mechanical stress, the measurements being performed at temperatures of not higher than 100 K below the glass transition temperature, a plurality of relaxation times of the glass or glass ceramic material being determined for a reference temperature based on said measurements, and weighting factors being determined, representing a weight of the plurality of relaxation times in the relaxation of the glass or the glass ceramic;

a time-delayed change of a temperature-dependent or stress-dependent time-delayed deformation being calculated as a function of a predefined change in temperature or stress based on the plurality of relaxation times and the weighting factors;

the thermal or mechanical deformation being extrapolated to the predefined allowable range of values using the plurality of relaxation times;

the extrapolated thermal or mechanical deformation being compared whether it is within the range of values; and the glass or glass ceramic material being chosen as the extrapolated value of time-dependent thermal or mechanical deformation is within the allowable range of values.

20. The glass or glass ceramic article according to claim 19, where the glass or glass ceramic article is a telescope mirror.

* * * * *